(12) United States Patent
Taussig et al.

(10) Patent No.: US 12,281,302 B2
(45) Date of Patent: Apr. 22, 2025

(54) ASSEMBLY OF LONG NUCLEIC ACIDS BY LIGATION USING INDEXED SPLINT OLIGOS

(71) Applicant: Agilent Technologies, Inc., Santa Clara, CA (US)

(72) Inventors: David Taussig, Sunnyvale, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 17/879,530

(22) Filed: Aug. 2, 2022

(65) Prior Publication Data

US 2023/0037679 A1 Feb. 9, 2023

Related U.S. Application Data

(60) Provisional application No. 63/228,448, filed on Aug. 2, 2021.

(51) Int. Cl.
*C12N 15/10* (2006.01)
(52) U.S. Cl.
CPC .............................. *C12N 15/1093* (2013.01)
(58) Field of Classification Search
CPC ............. C12N 15/1093; C12Q 1/6855; C12Q 2521/501; C40B 40/06
See application file for complete search history.

(56) References Cited

U.S. PATENT DOCUMENTS 6,495,318 B2 12/2002 Harney
10,538,796 B2 1/2020 Sampas et al.

FOREIGN PATENT DOCUMENTS

WO 2021127238 A1 6/2021

OTHER PUBLICATIONS

Lohman et al., Efficient DNA ligation in DNA-RNA hybrid helices by Chlorella virus DNA ligase, 2014, Nucleic Acids Research, 42(3), 1831-1844 (Year: 2014).*
Bang et al., Gene synthesis by circular assembly amplification, 2008, Nature Methods, 5, 37-39 (Year: 2008).*
Cleary et al., "Production of complex nucleic acid libraries using highly parallel in situ oligonucleotide synthesis" Nature Methods (2004) vol. 1, No. 3, pp. 241-248.
Leproust et al., "Synthesis of high-quality libraries of long (150mer) oligonucleotides by a novel depurination controlled process" Nucleic Acids Research (2010) vol. 38, No. 8, pp. 2522-2540.
Troll, C.J. et al., "A ligation-based single-stranded library preparation method to analyze cell-free DNA and synthetic bligos," BMC Genomics, vol. 20, No. 1. Dec. 27, 2019, pp. 1-14.
International Search Report and Written Opinion for PCT/US2022/039193 mailed on Nov. 8, 2022.

* cited by examiner

*Primary Examiner* — Jeremy C Flinders
(74) *Attorney, Agent, or Firm* — K&L Gates LLP

(57) ABSTRACT

The present disclosure relates to a method of assembling long nucleic acids by enzymatically ligating oligonucleotide molecules hybridized to an indexed splint oligonucleotide molecules. Also disclosed are oligonucleotide structures comprising an indexed splint oligonucleotide useful in performing the disclosed method.

19 Claims, 14 Drawing Sheets

Type a: Complex Library
Library sequences have little sequence similarity except peripheral primer binding sites (600 distinct UTR sequences).

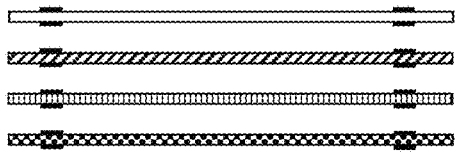

Type b: Tiled Library
Each member overlaps sequence identity with 3 other members by 82-246 base pairs. In this example there are 4 tiled constructs for each of 150 distinct UTR sequences.

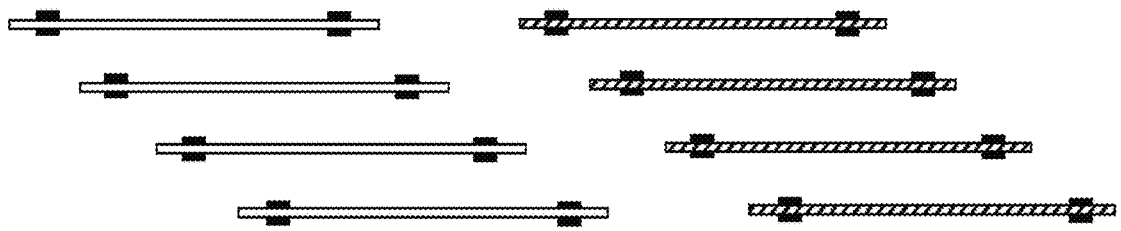

Type c: Homologous Library
In this example there are 10 uniquely barcoded constructs for each of 60 distinct UTR sequences.

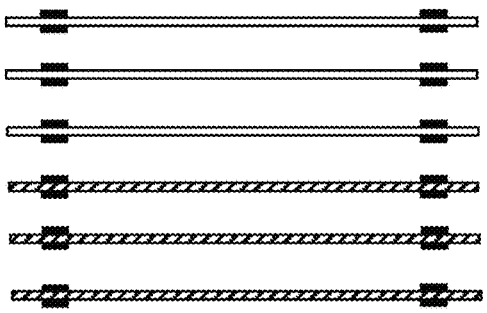

ASSEMBLY OF LONG NUCLEIC ACIDS BY LIGATION USING INDEXED SPLINT OLIGOS

CROSS-REFERENCE TO RELATED APPLICATION

The present application claims the benefit of priority to U.S. Provisional Application No. 63/228,448, filed Aug. 2, 2021, the entire contents of which is incorporated herein by reference in its entirety.

FIELD

The disclosure relates to the field of molecular biology. In particular, the present disclosure relates to a method for generating long nucleic acids, especially long DNA libraries.

BACKGROUND

DNA libraries are used in a wide range of applications in biology research as well as drug discovery. Currently, DNA libraries are most often generated by chemical synthesis of oligonucleotides ("oligos"), either in a massively parallel fashion on a solid surface or by pooling individually chemically synthesized oligos. One major limitation of these approaches is the length of DNA molecules that can be made by single-chain chemical synthesis. The longest commercially available oligo libraries currently have a maximum length of 350 nucleotides. However, many research applications such as gene synthesis, protein engineering, genome engineering and mutational saturation scanning would benefit from longer DNA libraries.

One approach to generating libraries of longer length involves enzymatic assembly of library members through the action of a DNA ligase joining two or more chemically synthesized oligos into longer constructs. Methods known in the field rely on single-stranded, compatible overhangs on specific double-stranded sequences to achieve specific annealing of the sequences in order to link the sequences in a predetermined order. See, for instance, U.S. Pat. No. 6,495,318. The '318 patent also discloses two specific sequences with terminal single-stranded portions that are hybridized to a single splint oligo having regions complementary to each piece. Under ideal conditions, the oligos appropriately hybridize to the splint, and a ligase joins the two pieces to form a longer construct. Methods similar to this are currently employed by various research groups with mixed success. The major drawback of this method is hybridization specificity, which can lead to poor quality libraries.

An alternative method for enzymatic assembly of long oligos involves hybridization of library pieces to a solid surface DNA array in order to spatially segregate constructs prior to ligation. See, e.g., U.S. Pat. No. 10,538,796.

In some aspects, the present invention addresses the need for a method that can be practiced in solution with high specificities for the sequences of interest.

BRIEF DESCRIPTION OF THE FIGURES

As shown in FIG. 5A, in this type of oligonucleotide structure, the indexed splint molecule comprises a splint sequence (splint) and two index sequences A and B (index sequence B and index sequence A). The two index sequences of the indexed splint molecule flank the splint sequence, with intervening spacer sequence spacer 1 and spacer 2 (dotted lines). The splint sequence has a 5' element and a 3' element, as depicted in the enlargement of the splint. The 5' element of the splint sequence hybridizes to the 5' end of the assembly component 2 oligonucleotide. The 3' element of the splint sequence hybridizes to the 3' end of the assembly component 1 oligonucleotide. One index sequence of the indexed splint molecule hybridizes to an index sequence at the terminus of one assembly component oligonucleotide. The other index sequence of the indexed splint molecule hybridizes to an index sequence at the terminus of the other assembly component oligonucleotide. FIGS. 5A and 5B illustrate two exemplary orientations for the indexed splint molecule to bind the two assembly components in the oligonucleotide structure. FIG. 5B depicts an orientation wherein a double-stranded index element (Index2) is formed by the hybridization of index sequence A (index sequence at the 5' end of the indexed splint molecule) to an index sequence at the 3' end of the assembly component 2. Double-stranded index element (Index1) is formed by the index sequence B (index sequence at the 3' end of the indexed splint molecule) hybridized to an index sequence at the 5' end of the assembly component 1. The 5' element of the splint sequence hybridizes to the 5' end of the assembly component 2 oligonucleotide. The 3' element of the splint sequence hybridizes to the 3' end of the assembly component 1 oligonucleotide. The intended ligation point is the junction of the assembly components. FIG. 5C depicts a second orientation wherein a double-stranded index element (Index1) is formed by the hybridization of index sequence A (index sequence at the 5' end of the indexed splint molecule) to an index sequence (segment C) at the 5' end of the assembly component 1. Double-stranded index element (Index2) is formed by the index sequence B (index sequence at the 3' end of the indexed splint molecule) hybridized to an index sequence (segment F) at the 3' end of the assembly component 1. The 5' element of the splint sequence hybridizes to the 5' end of the assembly component 2 oligonucleotide. The 3' element of the splint sequence hybridizes to the 3' end of the assembly component 1 oligonucleotide. The intended ligation point is the junction of the assembly components.

FIGS. 10-13 together illustrate schematically a variant aspect of the disclosed method. FIG. 10 illustrates an oligonucleotide structure in which the index sequences of the two assembly components are hybridized to a single splint ("index splint") that hybridizes to the two index sequences forming double-stranded Index 1 and Index 2.

FIG. 11 depicts the ligation product of the oligonucleotide structure of FIG. 10. FIG. 11 also illustrates an optional aspect wherein the index splint is biotinylated for attachment to a solid support or an Indexed array.

FIG. 12A depicts an oligonucleotide structure wherein the indexed splint is linked to the construct splint via a spacer ("optional tether"). This represents another embodiment of the claimed index splint molecule comprising 5' to 3' a first index sequence (binds index at 5' end of oligo 1 to form Index1); a second index sequence (binds index at 3' end of oligo 2 to form Index 2); a spacer (optional tether); a splint wherein the 5' element hybridizes to 5' end oligo 2 and the 3' element hybridizes to the 3' end of oligo strand 1. FIG. 12B depicts an oligonucleotide structure wherein a second splint molecule ("construct splint"), which is not linked to the Index sprint, is hybridized to the 3' and 5' ends of the assembly component. Also depicted is the optional aspect wherein the index splint is biotinylated for attachment to a solid support or an Indexed array.

FIG. 13 shows the ligation product of FIG. 12B. FIG. 13 also shows optional additional structural features on the assembly components of the ligation product. An optional restriction enzyme site is depicted at the 5' end of index splint. PBS 1 and BPS 1 represent (optional) primer binding sites useful for amplifying the assembly products.

FIG. 16 illustrates schematically three types of representative oligo libraries. The solid boxes represent unique barcodes flanking assembled constructs.

Figure 1:
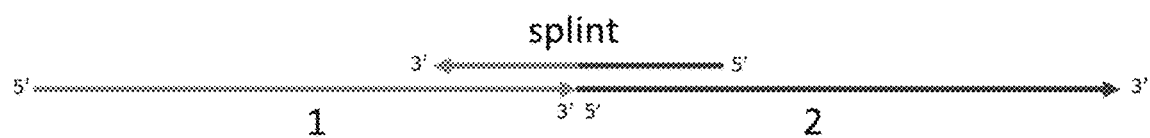
FIG. 1 depicts a type of oligonucleotide structure for assembling oligonucleotides into a multicomponent DNA construct. The oligonucleotide structure consists of two oligonucleotide pieces (1 is assembly component 1, the upstream assembly component, and 2 is assembly component 2, the downstream assembly component) hybridized to a single splint oligonucleotide (splint) having adjacent sequence regions complementary to each oligonucleotide piece. The arrowheads indicate the 3' ends of the oligonucleotides; the flat ends are the 5' ends of the oligonucleotides. The intended ligation point is the junction of assembly components 1 and 2.

The use of "half" in any of the figures or in the specification, e.g., "half construct left", is not intended to be limiting. For instance, a "half construct left" and a "half construct right" are not intended to indicate that assembly component 1 and assembly component 2 are the same length. The assembly components can differ in size. In this context, a "half" is comparable to a "portion", a "part", or an "oligonucleotide molecule."

DETAILED DESCRIPTION

This disclosure concerns, inter alia, a method for generating long DNA libraries in solution by enzymatically ligating oligonucleotides hybridized to indexed splint oligonucleotide molecules. In aspects, the oligonucleotides are chemically synthesized. The method is generally useful for producing long nucleic acids, including DNA or RNA, by ligating shorter components.

A. Definitions

As used herein, the singular forms "a", "an", and "the" include plural referents unless the context clearly dictates otherwise.

As used herein, the term "nucleic acid assembly" refers to a method of physically joining at least two nucleic acid fragments or oligonucleotides together in a specific order to create a desired nucleic acid sequence (a multicomponent construct), or the resulting nucleic acid of this process. Each of the fragments or oligonucleotides is an "assembly component" (sometimes colloquially referred to herein as "half construct"). When two assembly components are joined, the upstream component is the "upstream assembly component" (or assembly component 1 or left half construct or half construct left), and the downstream component is the "downstream assembly component" (or assembly component 2 or right half construct or half construct right). The 3' end of the upstream assembly component (assembly component 1) is joined with the 5' end of the downstream assembly component (assembly component 2). An assembly component comprises an assembly sequence and at least one non-assembly sequence. The "assembly sequence" is the sequence of interest, which is included in the final multicomponent construct. A non-assembly sequence refers to sequences related to the method of assembly, such as index sequences, primer sequences, restriction enzyme sequences, barcodes sequences, and the like.

As used herein, the term "5' terminal sequence" refers to an oligonucleotide sequence that includes the 5' terminus of a nucleic acid. As used herein, the term "3' terminal sequence" refers to an oligonucleotide sequence that includes the 3' terminus of a nucleic acid. A terminal sequence may contain 2 or more consecutive nucleotides, 3 or more, 5 or more, or 10 or more consecutive nucleotides, 30 or more consecutive nucleotides, 50 or more consecutive nucleotides, or 100 or more consecutive nucleotides. A 3' or 5' "substantially terminal sequence" refers to a sequence that is proximal to but does not include the 3' or 5' terminus. For example, the 3' or 5' end of the 3' or 5' substantially terminal sequence may be within about 100 nucleotides, within about 50 nucleotides, within about 30 nucleotides, within about 25 nucleotides, within about 20 nucleotides, within about 15 nucleotides, within about 10 nucleotides, within about 5 nucleotides, within about 4 nucleotides, within about 3 nucleotides, within about 2 nucleotides or within 1 nucleotide of the 3' or 5' terminal nucleotide, respectively.

The term "nucleic acid", "polynucleotide" or "oligonucleotide" refers to a DNA molecule, an RNA molecule, or analogs thereof. As used herein, the terms "nucleic acid", "polynucleotide" and "oligonucleotide" include, but are not limited to DNA molecules such as cDNA, genomic DNA or synthetic DNA and RNA molecules such as a guide RNA, messenger RNA or synthetic RNA. Moreover, as used herein, the terms include single-stranded and double-stranded forms.

The term "hybridization" or "hybridizing" refers to a process where completely or partially complementary polynucleotide strands come together under suitable hybridization conditions to form a double-stranded structure or region in which the two constituent strands are joined by hydrogen bonds. As used herein, the term "partial hybridization" includes where the double-stranded structure or region contains one or more bulges or mismatches. Although hydrogen bonds typically form between adenine and thymine or adenine and uracil (A and T or A and U respectively) or cytosine and guanine (C and G), other non-canonical base pairs may form (see, e.g., Adams et al., "The Biochemistry of the Nucleic Acids," 11th ed., 1992). It is contemplated that modified nucleotides may form hydrogen bonds that allow or promote hybridization in a non-canonical way.

As used herein, the term "portion", "segment", "element", or "fragment" of a sequence refers to any portion of the sequence (e.g., a nucleotide subsequence or an amino acid subsequence) that is smaller than the complete sequence. Portions, segments, elements, or fragments of polynucleotides can be of any length that is more than 1, for example, at least 5, 10, 15, 20, 25, 30, 40, 50, 75, 100, 150, 200, 300 or 500 or more nucleotides in length.

As used herein, the term "indexed splint" refers to an oligonucleotide comprising (1) a splint sequence that can hybridize to at least one target sequence, and (2) an index sequence that can hybridize to an index sequence in a target molecule. See, e.g., FIG. 5A. A "target" is an assembly component. Typically, an indexed splint is designed to hybridize to two targets in order to facilitate ligation of the two targets into a multicomponent construct. See, e.g., FIG. 5B. To that end, the splint sequence typically hybridizes to both targets and brings the 3' end of one target and the 5' end of the other target to proximity. The index sequence in the target is an extra sequence added into the target for the purpose of hybridizing to the index sequence in the indexed splint.

As used herein, the term "indexed splint-specific ordered ligation" refers to a protocol in which substantially single-stranded fragments are ligated to one another using a ligase to produce a multicomponent nucleic acid ligation product, where the order of fragments in the ligation product is directed by an indexed splint molecule comprising a splint that hybridizes to the 3' terminal sequence and 5' terminal sequence of the two fragments to be ligated. A "substantially single-stranded fragment" refers to a fragment that comprises partial double-stranded portions, such as a 3' or 5' terminal sequence hybridized to a splint sequence in an indexed splint molecule, and/or 3' or 5' terminal index sequence (or a 3' or 5' substantially terminal index sequence) hybridized to an index sequence in an indexed splint molecule.

An "index element" refers to a double-stranded DNA segment formed by (comprised of) two strands with sequences that are reverse complements of each other. An "index sequence" refers to a sequence, which is one of the two strands of sequences that are reverse complements of each other and form an index element by hybridization to each other. In some embodiments, the index sequence is not palindromic (e.g., no stem loop or other secondary structure). The two index sequences on a single indexed splint do not hybridize to each other.

The methods and products of the present disclosure are based, at least in part, on an unexpected discovery that utilizing an indexed splint molecule as schematically depicted in FIG. 5, panel A, results in improved assembly of multicomponent constructs in oligonucleotide libraries. By using indexed splint-specific ordered ligation, where each pair of assembly components to be ligated has a corresponding indexed splint molecule having a splint sequence and the index sequences specific for the pair of assembly components, assembly of multiple correct constructs in an oligonucleotide library is possible, even in homologous oligo libraries (oligo libraries in which the oligos share a substantial degree of sequence homology). The index sequences of the indexed splint molecule are not part of the construct sequence and thus are not affected by homology between library members. This is an unexpected benefit and improvement over previous high-throughput methods of multiplex assemblies.

As used herein, a "mixture of single-stranded oligonucleotides" refers to an aqueous solution that contains a plurality of different single-stranded oligonucleotides dissolved therein. A mixture may comprise at least 50, at least 100, at least 500 at least 1,000, at least 5,000, at least 10,000, or at least 50,000 or more of oligonucleotides, including any value in-between 50 and for example 50,000. A mixture of oligonucleotides may be made by synthesizing the oligonucleotides in situ, i.e., synthesizing the oligonucleotides in place in an array and then cleaving the oligonucleotides from the surface of the array after they have been synthesized. See, e.g., Geary et al. (*Nature Methods* 2004 1: 241-248) and LeProust et al. (*Nucleic Acids Research* 2010 38: 2522-2540).

The term "oligonucleotide" as used herein denotes a multimer of nucleotides. For example, an oligonucleotide may have about 2 to about 200 nucleotides, up to about 50 nucleotides, up to about 100 nucleotides, up to about 500 nucleotides in length, or any integer value between 2 and 500 in nucleotide number. In some embodiments, an oligonucleotide may be in the range of 30 to 300 nucleotides in length or 30 to 400 nucleotides in length. Oligonucleotides may contain ribonucleotide monomers (i.e., may be oligoribonucleotides) and/or deoxyribonucleotide monomers. An oligonucleotide maybe 10 to 20, 21 to 30, 31 to 40, 41 to 50, 51-60, 61 to 70, 71 to 80, 80 to 100, 100 to 150, 150 to 200, 200 to 250, 250 to 300, 300 to 350, or 350 to 400 nucleotides in length, for example, and any integer value in between these ranges.

As used herein, the term "a set of single-stranded oligonucleotides that can be assembled to produce a multicomponent ligation product" and grammatical equivalents thereof refers to a set of oligonucleotides that can be enzymatically assembled into a longer sequence, referred to herein as a "multicomponent construct" or "multicomponent ligation product", that contains sequences from each of the oligonucleotides in a defined order. As would be understood from the present disclosure, the single-stranded oligonucleotides of a set may contain: (i) a 3' or 5' terminal (or substantially terminal) sequence that is an index sequence that hybridizes to a complementary sequence in the indexed splint molecule to form a double-stranded index element, and (ii) an assembly sequence comprising a 5' or 3' terminal sequence that hybridizes to a splint sequence in an indexed splint molecule. The "assembly sequence" is the sequence of interest, which is included in the final construct, and does not include sequences related to the method of assembly, such as index sequences, primer sequences, restriction enzyme sequences, barcodes sequences, and the like.

As disclosed herein, a number of ranges of values are provided. It is understood that each intervening value between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

Other definitions of terms may appear throughout the specification.

B. Description of Methods and Products

One method for assembling specific oligonucleotides for enzymatic ligation to form a desired construct is depicted in FIG. 1. FIG. 1 depicts two oligonucleotides to be ligated, one being the upstream oligonucleotide ("assembly component 1") and the other one being the downstream oligonucleotide ("assembly component 2"). The upstream construct oligonucleotide is upstream (on a 5' to 3' basis) of the ligation point, and the downstream construct oligonucleotide is downstream of the ligation point. The upstream and downstream construct oligonucleotides are hybridized to a single splint oligonucleotide. The splint oligonucleotide has two regions of complementary sequences, one hybridizing to the upstream construct oligonucleotide and the other hybridizing to the downstream construct oligonucleotide, such that the 3' end of the left construct is immediately adjacent to the 5' end of the right construct to form the intended ligation site. Under hybridization conditions, the two assembly components hybridize to the single splint oligonucleotide, and a ligase joins the two pieces to form a longer, multicomponent construct.

In some embodiments, the disclosed method employs an indexed splint molecule comprising a splint region and two index sequences A and B (see, e.g., FIG. 5A) to assemble assembly components for ligation. The two index sequences of the indexed splint molecule flank the splint sequence, with intervening spacer sequences (dotted lines). The splint region has a 5' element and a 3' element, as depicted in the enlargement of the splint. The 5' element of the splint sequence hybridizes to the 5' end of the assembly component 2 oligonucleotide (see, e.g., FIG. 5B). The 3' element of the splint sequence hybridizes to the 3' end of the assembly component 1 oligonucleotide. In some aspects, the index sequences A and B are not palindromic (e.g., no stem loop or other secondary structure) and also do not hybridize to each other. One index sequence of the indexed splint molecule hybridizes to an index sequence at the terminus of one half construct. The other index sequence of the indexed splint molecule hybridizes to an index sequence at the terminus of the other half construct. Thus, with the splint sequence and index sequences both hybridizing to the two half constructs, the indexed splint brings the two half constructs to proximity, and aligns them in position for ligation.

The index sequences are not part of the sequence of interest. They are extra sequences added to the ends of both assembly components. As such, they can be designed as different from the other sequences in the reaction mixture as possible, thus reducing the chance of unintended pairs of assembly components, particularly when a plurality of different assembly components are ligated in the same reaction (i.e., multiplex).

The 3' element and the 5' element of the splint are each about 5 to 20 nucleotides in length and optionally have a melting temperature less than the melting temperature of the index elements. In some embodiments, the splint elements should not be sufficient alone (i.e., in the absence of the index elements) to drive hybridization under reaction conditions, but will only transiently hybridize when the assembly components are held in place through hybridization of the index sequences of the indexed splint to the two assembly components, in order to substantially reduce or eliminate unintended pairing of two assembly components. This is particularly important when the assembly components in the reaction share a substantial degree of homology (e.g., a homologous oligo library).

Figure 5A:
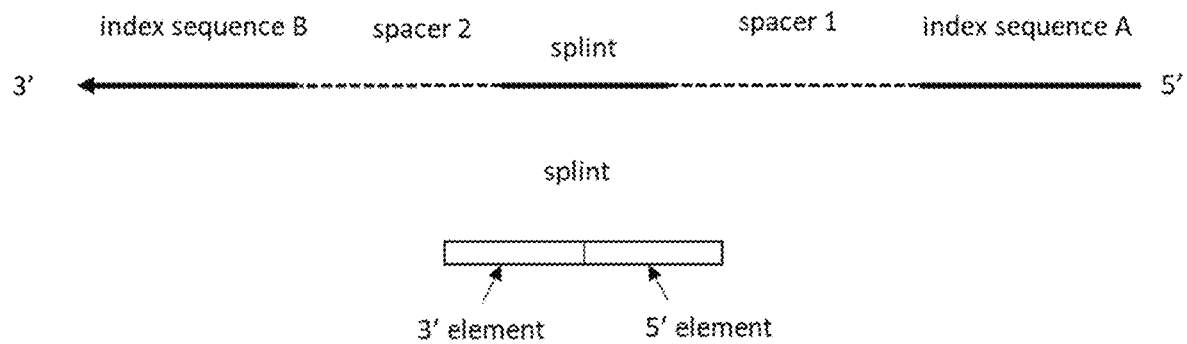
FIGS. 5A-5C depict another type of oligonucleotide structure for assembling oligonucleotides into a multicomponent DNA construct. The oligonucleotide structure comprises an indexed splint molecule (depicted in FIG. 5A) hybridized to two oligonucleotide pieces (assembly component 1 and assembly component 2). The arrow heads indicate the 3' end of the oligonucleotides; the flat ends are the 5' end of the oligonucleotides. Dotted lines represent an optional spacer sequence.
Figure 5B:
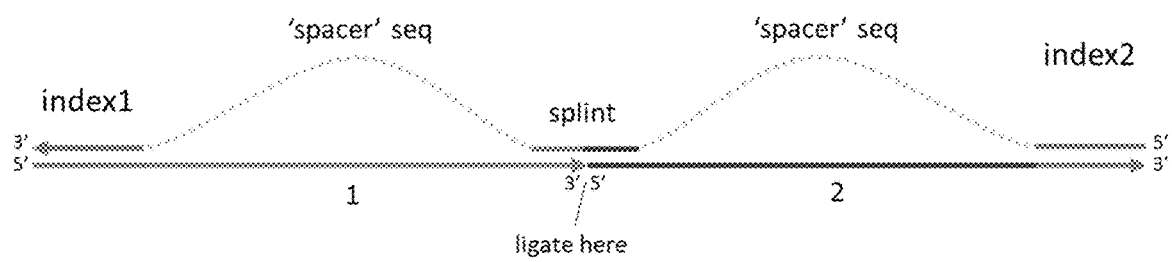
Figure 5C:
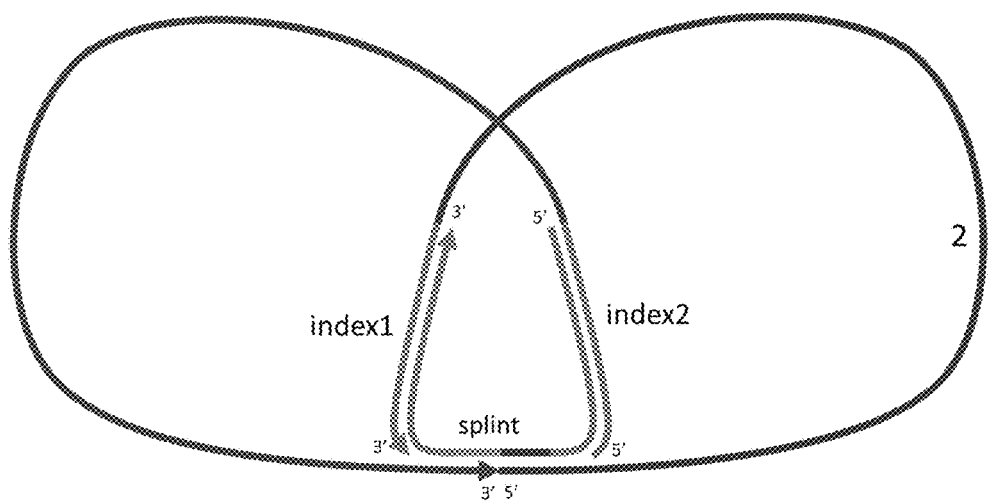

There are two exemplary orientations for the indexed splint molecule to bind the two assembly components in the oligonucleotide structure, as illustrated in FIGS. 5B and 5C.

FIG. 5B depicts an orientation wherein index sequence A (index sequence at the 5' end of the indexed splint molecule) hybridizes to an index sequence at the 3' end of the assembly component 2 forming a double-stranded index element (Index2). Index sequence B (index sequence at the 3' end of the indexed splint molecule) hybridizes to an index sequence at the 5' end of the assembly component 1 forming a double-stranded index element (Index1).

FIG. 5C depicts a second orientation wherein index sequence A (the index sequence at the 5' end of the indexed splint molecule) hybridizes to an index sequence at the 5' of the assembly component 1 forming a double-stranded index element (Index2). Index sequence B (the index sequence at the 3' end of the indexed splint molecule) hybridizes to an index sequence at the 3' of the assembly component 2 forming a double-stranded index element (Index1). Note that the indexed splint molecule is illustrated with a 180° twist to accommodate the 5' element of the splint hybridizing to the 5' end of the assembly component 2 oligonucleotide and the 3' element of the splint sequence bind hybridizing to the 3' end of the assembly component 1 oligonucleotide. The twist is for illustration purposes only and not intended to be limiting.

Exemplary advantages and distinguishing features of the present invention in assembly of polynucleotides into multicomponent construct include the following. The invention does not require an array or solid support for the assembly method. The method can be used to assemble single-stranded oligonucleotides. In one aspect, the method is carried out using synthetic oligonucleotides. In one aspect, the method is carried out using an oligonucleotide library comprising a mixture of single-stranded oligonucleotides. A mixture may comprise at least 50, at least 100, at least 500 at least 1,000, at least 5,000, at least 10,000 or at least 50,000 or more oligonucleotides. Additionally, in aspects, the method can be performed as an iterative process wherein the non-assembly sequences can be removed cleanly before the next cycle, like Type II restriction (i.e., the site of fragment joining is "scarless.") The method can be utilized to assemble complex libraries, low homology libraries, and high homology libraries, such as libraries having substantially identical sequences except for small variations.

Figure 2:
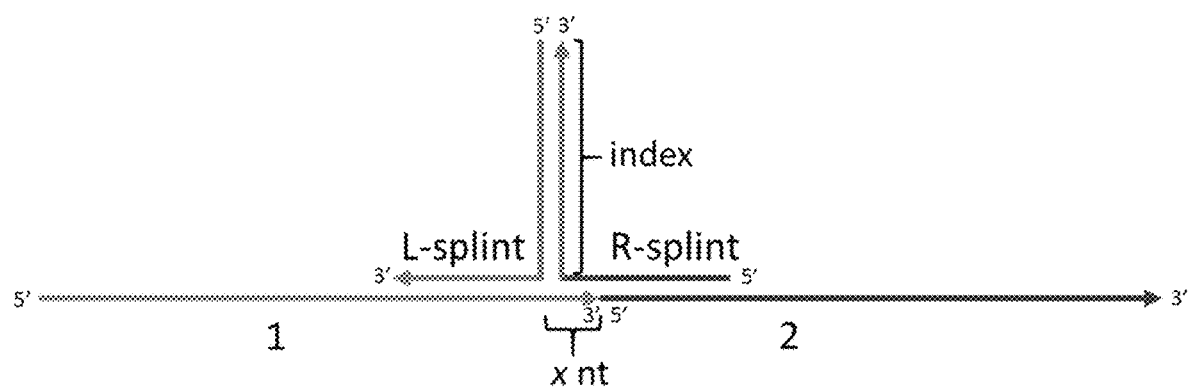
FIG. 2 depicts another type of oligonucleotide structure for assembling oligonucleotides into a multicomponent DNA construct. The oligonucleotide structure consists of two oligonucleotide pieces (assembly component 1 and assembly component 2) hybridized to an indexed splint structure. The indexed splint structure has a pair of splint oligonucleotide members. Each member of the pair has an index sequence that hybridizes to the other index sequence of the other member to form a double-stranded index element (index), thus serving to bring the two assembly components in close proximity to each other. One splint oligonucleotide member has a splint sequence region (L-Splint) complementary to the assembly component 1 oligonucleotide. The other splint oligonucleotide member has a splint sequence region (R-Splint) complementary to a 3' terminal portion of the assembly component 1 and to the 5' terminal portion of the assembly component 2 oligonucleotide. The arrowheads indicate the 3' end of the oligonucleotides; the flat ends are the 5' end of the oligonucleotides. The intended ligation point is the junction of the assembly components.

Indexed splints can be used in other manners. In one variation, shown in FIG. 2, two oligonucleotides representing the left and right halves of the intended construct are hybridized to a pair of splint oligonucleotide members. Each member of the pair of splint oligonucleotide members further contains an index sequence that is a reverse complement of the index sequence in the other member of the pair, and thus able to hybridize to each other and form a double-stranded DNA portion referred to herein as an index element (labeled "Index" in FIG. 2). The two index sequences serve indirectly to bring together the two assembly components. The index sequences are not part of the assembly sequence itself. In FIG. 2, the right indexed splint contains a splint sequence (R-Splint) homologous to the 3' end of the left construct oligonucleotide and a section homologous to the 5'-end of the right construct oligonucleotide. In FIG. 2, R-Splint contains about 10 nucleotides (nt), but it can range, e.g., from about 5 nt to about 20 nt.

Figure 3:
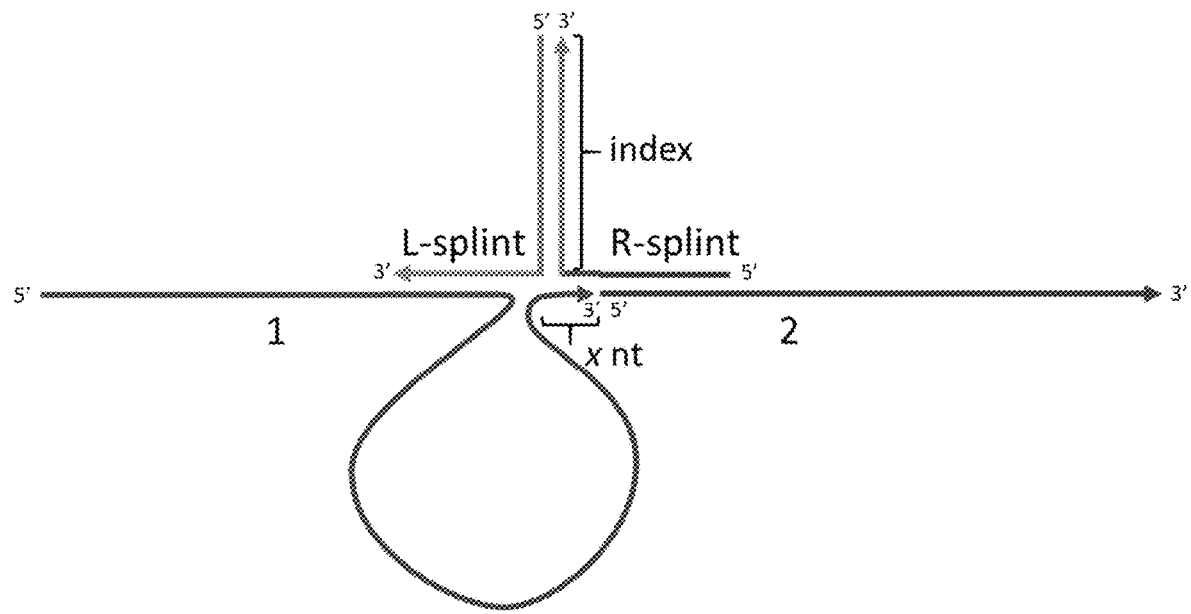
FIG. 3 depicts another type of oligonucleotide structure for assembling oligonucleotides into a multicomponent DNA construct. The oligonucleotide structure consists of two oligonucleotide pieces (assembly component 1 and assembly component 2) hybridized to an indexed splint structure, similar to the structure in FIG. 2. The indexed splint structure has a pair of splint oligonucleotide members. Each member of the pair has an index sequence that hybridizes to the other index sequence of the other member to form a double-stranded index element. In this structure, the splint oligonucleotide member has a splint sequence region (L-Splint) complementary to a sequence in the assembly component 1 oligonucleotide that is not proximal to the 3' end of the assembly component 1 oligonucleotide, resulting in a looped portion of the assembly component 1. The other splint oligonucleotide member has a splint sequence region (R-Splint) complementary to a 3' terminal portion of the assembly component 1 and to the 5' terminal portion of the assembly component 2 oligonucleotide. The arrowheads indicate the 3' end of the oligonucleotides; the flat ends are the 5' end of the oligonucleotides. The intended ligation point is the junction of the assembly components.

All splint sequences do not have to hybridize to terminal sequences of the target. Another variation of an indexed splint is illustrated in FIG. 3. This oligonucleotide structure is a variant of the FIG. 2 oligonucleotide structure. The inventors contemplated that this structure could reduce or eliminate interference caused by truncated synthesis products lacking the 5' end of the designed assembly components. In this structure, the splint oligonucleotide member has a splint sequence region (L-Splint) complementary to a sequence in the assembly component 1 oligonucleotide that is not proximal to the 3' end of the assembly component 1 oligonucleotide, resulting in a looped portion of the assembly component 1. The other splint oligonucleotide member has a splint sequence region (R-Splint) complementary to a 3' terminal portion of the assembly component 1 and to the 5' terminal portion of the assembly component 2 oligonucleotide.

Figure 4:
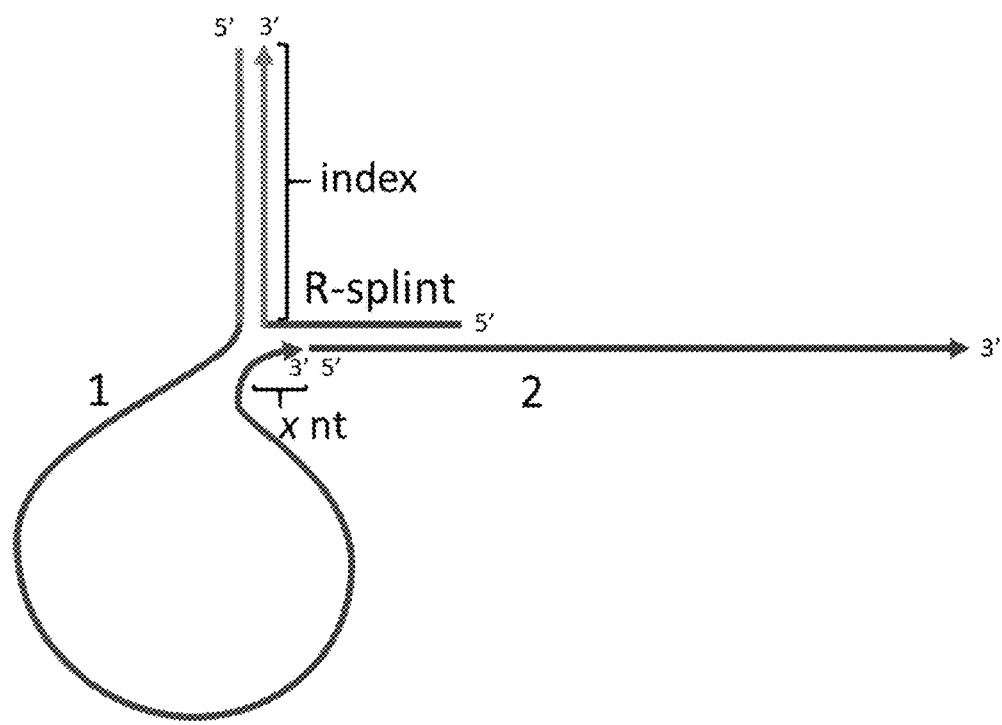
FIG. 4 depicts another type of oligonucleotide structure for assembling oligonucleotides into a multicomponent DNA construct. The oligonucleotide structure consists of two oligonucleotide pieces (assembly component 1 and assembly component 2) hybridized to a single indexed splint molecule. In this structure, the assembly component 1 oligonucleotide has a 5' index sequence 5' to the assembly sequence. The index sequence hybridizes to the index sequence of the indexed splint molecule to form a double-stranded index element. The splint oligonucleotide member has a sequence region (R-splint) complementary to a sequence in the assembly component 1 oligonucleotide at the 3' end the assembly component 1 oligonucleotide, and to the 5' terminal portion of the assembly component 2 oligonucleotide, resulting in the looping of the assembly component 1 (somewhat similar to FIG. 3). The arrow heads indicate the 3' end of the oligonucleotides; the flat ends are the 5' end of the oligonucleotides. The intended ligation point is the junction of the assembly components.

In FIG. 4, the assembly component 1 oligonucleotide has a 5' index sequence at the 5' end assembly component 1. The index sequence hybridizes to the index sequence of the indexed splint molecule to form a double-stranded index element. The splint molecule has a sequence complementary to in the 3' terminal portion of the assembly component 1 assembly component 1, and to the 5' terminal portion of the assembly component 2 oligonucleotide, resulting in the looping of the assembly component 1 (similar to FIG. 3, but only one indexed splint is used).

As shown herein, embodiments such as the ones illustrated in FIGS. 5A-5C provided notable advantages. Assembly of low homology library or a complex library using the FIG. 5 indexed splint molecule yielded high accuracy (i.e., total number of correct reads relative to the total number of reads). See FIG. 17. "Complex library" refers to library sequences that have little sequence similarity except peripheral primer binding sites. In addition, there were no dropout constructs. Thus, the data indicate that assembling assembly components using the indexed splint molecule of FIG. 5 enables much higher discrimination. Accordingly, the invention enables correct assembly of constructs that would otherwise be impossible due to promiscuous hybridization of a splint molecule, such as that in FIG. 1.

Thus, this disclosure provides a method for assembling a multicomponent construct utilizing specific oligonucleotides employing an indexed splint for enzymatic ligation. The disclosure provides, among other things, a method for assembling two or more specific components by indexed splint-specific ordered ligation to form a multicomponent ligation product having a pre-defined order. The method can be conducted in solution and in the absence of solid support. The method may be used to produce a synthetic multicomponent construct by ligating sequences from two, three or four or more single-stranded oligonucleotides in a defined order. The method may be multiplexed in that a plurality of different synthetic multicomponent constructs (e.g., at least 2, at least 10, at least 100, at least 1,000 or at least 10,000, or at least 100,000 multicomponent constructs) can be produced in the same solution. This process can also be repeated several times to produce longer nucleic acids.

In certain embodiments, the oligonucleotide molecules are produced by chemical synthesis using methods well-known in the art of synthetic organic chemistry. Some oligonucleotides molecules described herein can alternatively be made using methods known in the art that include in vitro transcription and cell-based expression.

The various oligonucleotide molecules used in the method of the disclosure as well as the methods are described in more detail in the following disclosure.

Indexed Splint

In some embodiments, the methods of the disclosure employ an indexed splint as illustrated in FIG. 5A. The indexed splint comprises a splint region, a first index sequence, and a second index sequence. In some embodiments, the first index sequence and the second index sequence flank the splint region. The first index sequence and the second index sequence may be located at the 5' and 3' end of the indexed splint. In one aspect, one or both of the first index sequence and the second index sequence comprise terminal sequences (e.g., the 5' terminal sequence and/or the 3' terminal sequence) of the indexed splint. In some embodiments, one or both of the first index sequence and the second index sequence comprise substantially terminal (e.g., the 5' substantially terminal sequence and/or the 3' substantially terminal sequence) of the indexed splint but not the terminal nucleotide. The splint region has a 5' sequence element and a 3' sequence element, which hybridize to each of the two assembly components, respectively, and bring the ends of the assembly components to proximity. As illustrated in FIGS. 5A-5C, the 5' element of the splint sequence hybridizes to the 5' end of the downstream assembly component (assembly component 2), while the 3' element of the splint sequence hybridizes to the 3' end of the upstream assembly component (assembly component 1). As a result, the 5' end of the downstream assembly component and the 3' end of the upstream assembly component are brought together and can be ligated by a ligase.

There are two exemplary orientations for the indexed splint molecule to bind the two assembly components in the oligonucleotide structure for ligation, shown in FIGS. 5B and 5C, respectively.

The index sequences are not part of the sequence of interest, and will not appear in the final assembly. They are extra sequences added to the ends of both assembly components. As such, they can be designed as different from the other sequences in the reaction mixture as possible, thus reducing the chance of unintended pairs of assembly components, particularly when a plurality of different assembly components are ligated in the same reaction (i.e., multiplex).

Features of an index element include the following. The index sequences are designed to hybridize only to their complement. Thus, for any given index element, neither sequence (complement or reverse complement) is present in the final construct molecule. Similarly, for indexed splint molecules comprising one or more spacer sequences, neither index sequence (complement or reverse complement) is present in the spacer. The index sequences are preferably designed to not have stable secondary structure by itself, such as stem-loop structure, and therefore are not palindromic. Moreover, the nucleotide composition of the index element is preferably designed to have a suitable melting temperature (Tm) for use in the method of assembly. In some embodiments, the index element is designed to remain hybridized in temperature ranges in which the splint elements can only transiently hybridize to the assembly component except for splint elements with 100% identity to a assembly component. Mismatches in a splint element sequence to a construct element destabilize hybridization. It is believed, without being held to theory, that this dynamic hybridization permits sampling that favors formation of splint element-to-assembly component hybridization of 100% identity. It is believed that this contributes to the high accuracy of multicomponent constructs formed in the method of the disclosure. In some aspects, assembly accuracy (i.e., total number of correct reads relative to the total number of reads) is at least 80%, 85%, or at least 90%, such as at least 91%, 92%, 93%, 94%, 95% or at least 96%. It is also believed, without being held to theory, to contribute to a low-to-no drop out of intended constructs and thus provide a high percentage of intended constructs represented. In some aspects, the percentage of the intended constructs is at least 80%, 85%, or at least 90%, such as at least 91%, 92%, 93%, 94%, 95%, 96%, 97% or at least 98% of the total number of intended constructs.

Optionally, index sequences are random, high complexity sequences that are base balanced (A=T=G=C) to help predict the melting temperature. Homopolymer repeats can be included. In other embodiments, index sequences do not include repetitive elements, such as homopolymers and/or dinucleotide repeats, e.g., GTGTGTGT. High melting temperatures are useful in the practice of the disclosed method. The Tm of each index sequence can be from about 50° C. to about 80° C., from about 65° C. to about 72° C., from about 55° C. to about 75° C., from about 50° C. to about 70° C., or from 60° C. to about 80° C. In an aspect, the Tm of each index sequence is about 65° C. to about 69° C. In an aspect, the Index sequences can be from 20 nt to 60 nt. Index sequences can be from 20 nucleotides (nt) to 50 nt, 25 nt to 45 nt, from 25 to 35 nt, or from 28 nt to 32 nt. In an aspect, index sequences are about 30 nucleotides. A reason to keep the index sequence shorter is to maximize construct sequence length in assembly components. The main impediments to making very short index sequences is that specificity and duplex stability are degraded. Index sequences can be prepared as a library of sequences. Potential index sequences are screened against an appropriate genome to exclude sequences that might hybridize. In an aspect, a potential index sequences are screened against the human genome. Index sequences in a library of sequences may be designed to share some features such as length, base balance, or melting temperature, while being designed to disfavor hybridization between different index sequences. In an aspect, a library of sequences may contain multiple sets or of index sequences which share features within a set, while being different from other sets. For example, a library of sequences may comprise one set of index sequences designed with one predicted melting temperature, while a second set of index sequences within the library may be designed with a different melting temperature.

Splint

The indexed splint comprises a splint sequence. The splint sequence is intended to guide specificity of pairing of two assembly components. As illustrated in FIG. 5A, the splint sequence (splint) has two sequence elements: a 5' element (5'-element) and a 3' element (3' element). The 5' element of the splint sequence hybridizes to the 5' end of the downstream assembly component. More specifically, the 5' element hybridizes to 5' terminal or 5' substantially terminal sequence of the downstream assembly component (assembly component 2) (see, e.g., FIG. 5B). The 3' element of the splint sequence hybridizes to the 3' end of the upstream assembly component (assembly component 1). More specifically, the 3' element hybridizes to 3' terminal or 3' substantially terminal sequence of segment D of the upstream assembly component (assembly component 1) (see, e.g., FIG. 5B).

Splints are typically short sequences or sequences with a melting temperature lower than the melting temperature of the index regions. In some embodiments, each splint element is designed to be insufficient in itself to drive hybridization under reaction conditions. Instead, the splint sequence is designed to only transiently hybridize to the assembly component oligonucleotide when the assembly components are held in place through hybridization to the index sequences of the indexed splint oligonucleotide. In an aspect, the 5' element and the 3' element of the splint sequence are contiguous, without intervening nucleotides. In an aspect, the 5' element and the 3' element of the splint sequence are substantially contiguous, e.g. an intervening few (one, two or three) nucleotides are present between the 5' element and the 3' element, and the intervening few nucleotides are not intended to bind to either assembly sequence of the assembly components. The 5' element and the 3' element of the splint sequence can be independently about 5 nucleotides to about 25 nucleotides in length, or about 5 nucleotides to about 20 nucleotides in length, or about 8 nucleotides to about 15 nucleotides, or about 10 nucleotides to 13 nucleotides in length. The 5' element and the 3' element of the splint generally have similar melting temperatures. The melting temperatures of the splint elements are less than the melting temperatures of the index elements. The choice of melting temperature of the splint elements is influenced by the ligase used in the assembly step. In some aspects, melting temperature (Tm) of the splint elements, when calculated by $Tm=(2*(A_{count}+T_{count}))+(4*(C_{count}+G_{count}))-7$, can be in the range of 10° C. to 80° C., from 14° C. to 44° C., from 20° C. to 42° C., or from 22° C. to 40° C. The skilled artisan will recognize that different splint melting temperatures may be chosen for different ligases, for example, a ligase that can be used at a higher temperature e.g. a thermostable ligase, such as 9° N™ DNA Ligase (New England Biolabs, Ipswich, MA) may be used with splints having a higher melting temperature.

In some aspects, the indexed splint comprises spacer sequences, which are linkers between specific structural features (e.g., index sequences and splint sequence) of an indexed splint. Spacers can be from 1 to 30 nucleotides in length in some embodiments. A spacer is any sequence or non-nucleic acid component, which is designed to not hybridize to assembly sequences or to index sequence. In some embodiments, spacer may be a simple sequence such as a homopolymer sequence or a short repeated sequence, such as a di- or tri-nucleotide repeat. In some aspects, an indexed splint has two spacer sequences, as illustrated in FIG. 5A. In some aspects, an indexed splint has more than two spacer sequences to link one or more additional structure features. For instance, as discussed elsewhere herein, an indexed splint for an iterative assembly application may contain a second splint element and a third index sequence, wherein spacer sequences can optionally separate the specific structural features.

Assembly Components

In some embodiments, an assembly component is an oligonucleotide molecule that comprises a sequence desired to be in the final construct assembly, and an index sequence. The location of the index sequence in an assembly component depends on whether the component is the left (upstream) component or the right (downstream) component in the intended ligation reaction.

Typically, in the upstream assembly component, the indexed splint sequence is located at the 5' terminal or substantially at the 5' terminal of the assembly component oligonucleotide. The assembly sequence is located at the 3' terminal region of the assembly component oligonucleotide. In an aspect, the index sequence is contiguous with the assembly sequence. In other aspects, additional sequences (structural features) may be located between the index sequence and the assembly sequence. Such structural features may be one or more of the following: at least one primer sequence, at least one barcode sequence, and/or at least one restriction enzyme cleavage site. In aspects, a Type IIS restriction enzyme site is immediately upstream of the assembly sequence. See, e.g., FIG. 8, molecule (c). In this aspect, the Type IIS restriction enzyme site is positioned such the enzymatic cleavage at the cleavage site separates all of the non-assembly sequence from the assembly sequence. This aspect is useful for iterative versions of the method, for instance, wherein the product of a first assembly step is then used as a component in a subsequent assembly step.

Typically, in the downstream assembly component, the indexed splint sequence is located at the 3' terminal or substantially at the 3' terminal of the assembly component oligonucleotide. The assembly sequence is located at the 5' terminal sequence of the assembly component oligonucleotide. In an aspect, the index sequence is contiguous with the assembly sequence (Segment E). In other aspects, additional sequences may be located between the assembly sequence (Segment E) and the index sequence (segment F). Such sequences may be one or more of the following: at least one primer sequence, at least one barcode sequence, and at least one restriction enzyme cleavage site. In aspects, a Type IIS restriction enzyme site is immediately downstream of the assembly sequence. See, e.g., FIG. 8, molecule (a). The Type IIS restriction enzyme site is positioned such the enzymatic cleavage at the cleavage site removes all of the non-assembly sequence from the assembly sequence. This aspect is useful for iterative versions of the method. This aspect is useful for iterative versions of the method, for instance, wherein the product of a first assembly step is then used as a component in a subsequent assembly step.

Methods

The disclosure provides a method for assembling two nucleic acid assembly components to produce a ligation product (multicomponent assembly). In some embodiments, the method comprises hybridizing an upstream assembly component and a downstream assembly component to an indexed splint present in a reaction mixture. In some embodiments, in the hybridized structure, both the 5' end and the 3' end of the upstream assembly component are hybridized to the indexed splint and both the 5' end and the 3' end of the downstream assembly component are hybridized to the indexed splint. The hybridizing step is followed by a ligating step. In the ligating step, the 3' end of the upstream assembly component is ligated to the 5' end of the downstream assembly component, thereby producing a first ligation product. In an aspect, the reaction mixture is multiplexed and comprises a mixture of single-stranded oligonucleotides comprising a plurality of upstream assembly component species, a plurality of downstream assembly component species, and a plurality of indexed splint molecule species. Each of the plurality of indexed splint molecule species can hybridize to a pre-determined upstream assembly component and a pre-determined downstream assembly component in the mixture.

The method is carried out in an aqueous solution. The aqueous solution can be the same for both the hybridizing step and the ligating step. The aqueous solution for the ligation step can be any aqueous solution having suitable pH and salt concentration that is suitable for the ligase used in the method. The reaction solution is typically buffered and comprises one or more salts and may optionally comprise a molecular crowding agent such as PEG (polyethylene glycol), as suitable for the ligase. In some embodiments where the same aqueous solution is used for both the hybridization and ligation steps, the components of the buffer may be chosen to be more or less favorable for the ligase enzyme, or more or less favorable for the hybridization reaction, to achieve the best results. For example, the concentration of magnesium in the solution may be chosen to be either slightly lower, or significantly higher than what is ideal for the ligase reaction, if that concentration of magnesium supports a more stringent hybridization step.

The hybridization step can be carried out by incubation in a water bath cooling the reaction from an elevated temperature to a cooler temperature over a period of time sufficient to form the oligonucleotide structures comprising an indexed splint and two assembly components. The temperature profile of the hybridizing step is guided by the Tm of the index sequences and the Tm of the splint regions. For instance, the hybridization step may begin at a higher temperature, followed by a cool down period. The starting temperature exceeds the Tm of the index sequences to melt out any secondary structure. An exemplary temperature profile is from about 95° C. to about 40° C., such as 93° C. to 44° C. The duration of the hybridization cooling down can range from about 15 minutes to several hours. An exemplary duration is 1.75 hours. In an aspect, the hybridization step comprises cooling from 93° C. to 44° C. over 1.75 hours. In some embodiments, the temperature of the hybridization step may be varied over time or cycled from a higher to a lower temperature over several cycles.

The ligation step is carried out by contacting the hybridized oligonucleotide structures with a ligase. The temperature of the reaction mixture can be altered to the appropriate temperature for the ligase to be used, and in some embodiments the temperature is below the melting temperature of the index elements and above the melting temperature of the splint elements. For instance, after hybridization, the temperature of the reaction mixture is increased to a range of about 45° to about 70° C., about 45° to 65° C., about 50° to 65° C., or about 61° C. to 65° C., etc., then the hybridized oligonucleotide structures are contacted with a thermostable ligase. Lower temperatures can be used for a non-thermostable ligase. The ligation step is carried out for a suitable length of time, which can range from minutes to hours. Optionally, the ligation step is terminated by a method known in the art. For instance, the ligase can be denatured by high temperature, by a chemical denaturant, or EDTA could be added (to bind the magnesium needed for the ligation reaction.)

The method can be carried out with any ligase. DNA and RNA ligases are commercially available. Alternatively, the ligase can be chemically synthesized (see e.g., Creighton, PROTEINS: STRUCTURES AND MOLECULAR PRINCIPLES, 2nd Edition, W. H. Freeman & Co., NY, 1992) or can be made recombinantly via molecular biology methods such as expression in cells. A recombinant ligase can be prepared as a fusion protein, for instance, to aid purification.

In certain aspects, the ligase is provided in purified or isolated form. In certain embodiments, the ligase is provided at about 80%, about 90%, about 95%, or about 99% purity. In certain embodiments, the ligase is provided as part of a composition. In certain embodiments, the ligase is provided in aqueous compositions suitable for use as, or inclusion in, a composition for assembly of multicomponent constructions. Those of skill in the art are well aware of the various substances that can be included in such ligase reaction compositions.

The choice of ligase will impact the temperature of the ligating step. Different ligases may have different efficiencies, different activities at different temperatures, and different sensitivities to mismatches at the ligation site. There are many examples of mesophilic DNA ligases that function at lower temperatures ranges. Thermostable ligases are also available. Thermostable ligases permit ligase reaction conditions at higher temperature, e.g., up to 65° C. Higher temperature reaction conditions can contribute to more accurate assembled constructs. In an aspect, the thermostable ligase has a bigger footprint requirement (e.g., about 25 nucleotides hybridized sequence) before ligation occurs at the ligation site. This feature can contribute to greater specificity, resulting in better purity of the ligated products. In an aspect, multiple ligases may be used. In an aspect, different ligases may be added sequentially to the same hybridization reaction. In an aspect, different ligases may be included in the same reaction. For example, a mesophilic ligase and a thermostable ligase may be included in the reaction, and the mesophilic ligase could be used at a lower temperature, before the temperature is raised for the thermophilic ligase. Such embodiments can be applicable with practicing the method with a library of sequences comprising one set of index sequences designed with one predicted melting temperature, while a second set of index sequences within the library may be designed with a different melting temperature.

The concentration of the oligonucleotide components is a reaction parameter that influences ligation accuracy. High concentrations of the oligonucleotide components increase the possibilities for wrong ligation results. Thus, lower concentrations can result in improved accuracy of the ligation product.

Generally, the hybridization conditions, lengths of hybridized sequences, and ligation conditions may be varied to achieve the highest yield of accurately assembled constructs. For example, if a set of conditions leads to inaccurate assemblies for a particular set of components, a higher ligation temperature and/or more stringent hybridization condition may be used. Optimizing the hybridization conditions and the ligase conditions is within the scope of the skilled artisan, in view of the present disclosure and conventional knowledge in the art. See, e.g., Sambrook et al., *Molecular Cloning A Laboratory Manual*, 2<sup>nd</sup> Ed. Cold Spring Harbor Press (1989) or Anderson, *Nucleic Acid Hybridization*, 1st Ed., BIOS Scientific Publishers Limited (1999).

Figure 6:
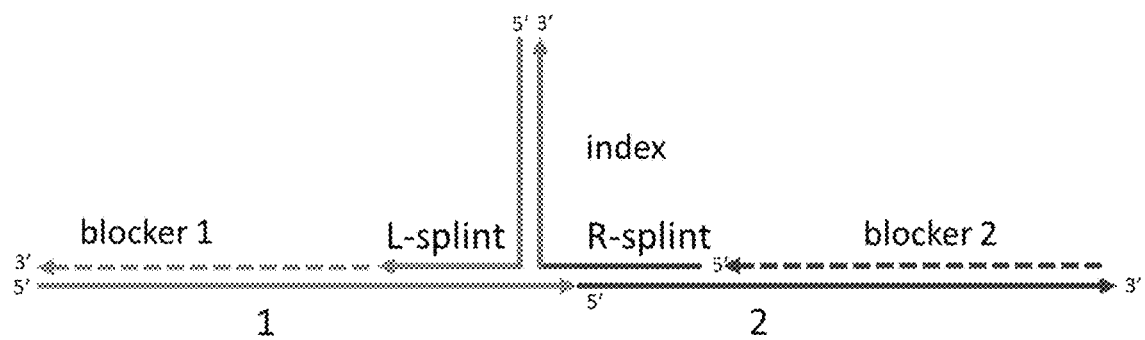
FIG. 6 illustrates a variation on FIG. 2 wherein the oligonucleotide structure comprises at least one blocking oligonucleotide (e.g., blocker 1) that can be hybridized to a region of the assembly sequence that does not hybridize to the splint. Two blocking oligonucleotides (blocker 1 and blocker 2) are depicted in FIG. 6. The arrow heads indicate the 3' end of the oligonucleotides; the flat ends are the 5' end of the oligonucleotides. The intended ligation point is the junction of the assembly components. One or more blocking nucleotides can be utilized in the oligonucleotide structures of FIGS. 5B and 5C.

In an aspect, the method can be carried using the indexed splint of FIG. 2 and further comprising at least one blocking nucleotide. FIG. 6 illustrates an oligonucleotide structure, wherein the oligonucleotide structure comprises at least one blocking oligonucleotide hybridized to single-stranded regions in the assembly sequence of the assembly components. This variation is contemplated to prevent unintended hybridization. Blocking oligonucleotides may be designed to block part or all of the single-stranded regions. In the depicted embodiment of FIG. 6, the oligonucleotide structure comprises two further oligonucleotide strands, one hybridizing to assembly component 1 sequence and one hybridizing to the assembly component 2 sequence. It is contemplated that the blocking oligonucleotides can be synthesized as part of the two oligonucleotide molecules of the indexed splint molecule depicted in FIG. 6. Blocking oligonucleotides can also be employed in the oligonucleotide structures of FIG. 5 or other embodiments of the present invention. It is contemplated that the blocking oligonucleotides can be synthesized as part of the indexed splint molecule depicted in FIG. 5.

The method can be carried out iteratively. In an aspect, the downstream assembly component comprises a removable (detachable) index sequence at the 3' end. After the hybridization and ligation steps to provide a ligation product comprising the assembly component, the index sequence is removed (e.g., via enzymatic cleavage or cleavage of a cleavable linker), such that the 3' terminal sequence of the ligated product is the 3' sequence of the assembly sequence. This first ligated product is then available as the upstream assembly component in another iteration of the method to produce a second ligated product. The reaction mixture comprises indexed splint molecules that hybridize to the first ligated product and to another downstream assembly component.

In an aspect, a removable (or detachable) index sequence comprises a restriction enzyme site. In an aspect, the restriction enzyme site is for a Type IIS restriction enzyme. Type IIS restriction enzymes comprise a specific group of enzymes that recognize asymmetric DNA sequences and cleave at a defined distance outside of their recognition sequence, usually within 1 to 20 nucleotides. This specific mode of cleavage action of Type IIS restriction enzymes permits cleavage such that the desired assembly sequence is retained and non-assembly sequence is removed. This permits DNA manipulation that does not alter the final assembly sequence and thus enables the generation of scarless joints in the multicomponent construct.

In an aspect, a removable (or detachable) index sequence can be an index sequence that is linked to an assembly sequence by a cleavable linker. Photocleavable linker chemistries are known in the art and are commercially available from TriLink Biotechnologies, Integrated DNA Technologies, and Glen Research.

Figure 7:
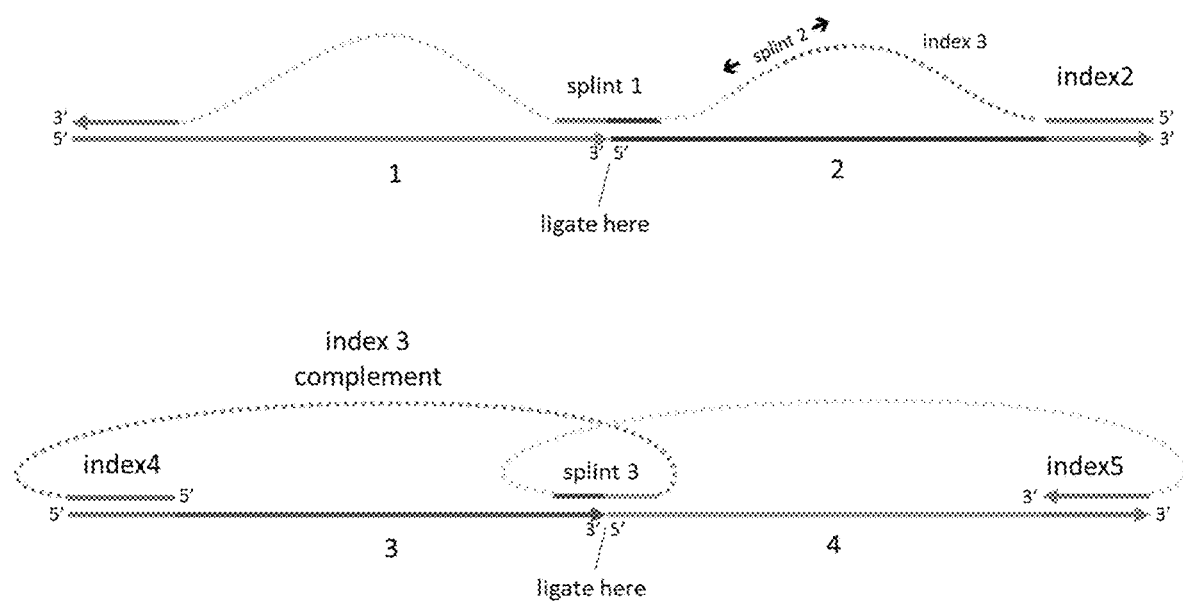
FIG. 7 depicts two oligonucleotide structures to be ligated in the first ligation step of a 4-part assembly process. (See also FIGS. 8 and 9). The first ligation step assembles assembly components 1+2 (top structure) and assembly components 3+4 (bottom structure) in separate reactions in a mechanism similar to 2-part assembly. The arrow heads indicate the 3' end of the oligonucleotides; the flat ends are the 5' end of the oligonucleotides. The intended ligation point in each oligonucleotide structure is indicated. In addition to the first splint structure (splint1), the indexed splint of the top oligonucleotide structure comprises a second splint sequence (splint2) in the spacer section and another index sequence (Index3) between the 5' index sequence (Index2) and the first splint structure (splint1). The indexed splint of the bottom oligonucleotide structure comprises a complementary sequence of Index3 (Index3 complement) between the first splint structure (splint3) and the 5' index sequence (Index4).
Figure 8:
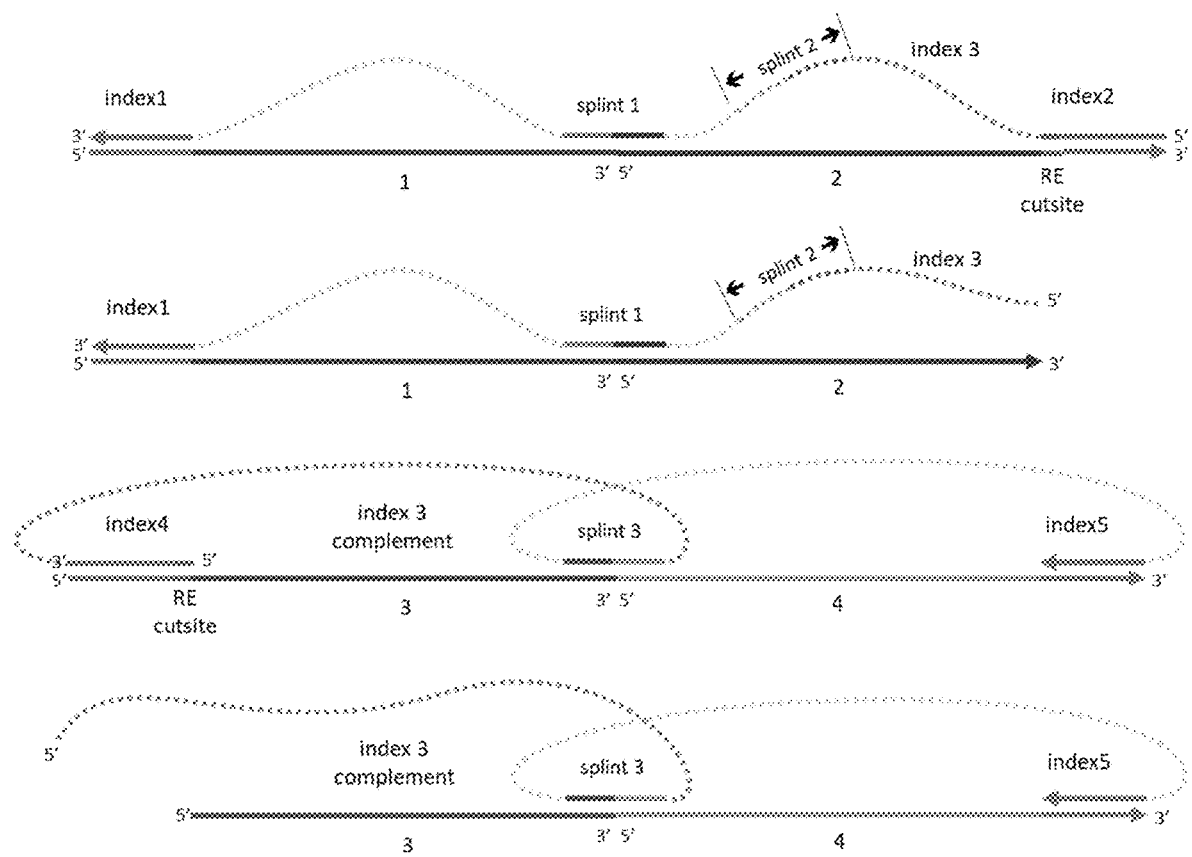
FIG. 8 depicts the next step of a 4-part assembly process. The ligation products of the assembly step depicted in FIG. 7 are illustrated in FIG. 8. Ligation yields two multicomponent ligation products, assembled product (1-2) (depicted in (a)) and assembled product (3-4) (depicted in (c). Also depicted is a Type IIS restriction enzyme cleavage site (RE cut site) located between the index sequence and assembly component for assembled product (1-2) and assembled product (3-4). The ligation products of the assembly step depicted in FIG. 7 are each subjected to digestion with a Type IIS restriction enzyme, to cleave at the RE cleavage site (not shown in FIG. 7). In the ligation product in (a), the cleavage removes Index2, leaving only assembly component sequence at the 3' end in assembled product (1-2), as illustrated in (b). In the ligation product in (c), the cleavage removes Index4, leaving only assembly component sequence at the 5' end in assembled product (3-4) as illustrated in (d). The resulting products are purified, for instance, by SPRI purification.
Figure 9:
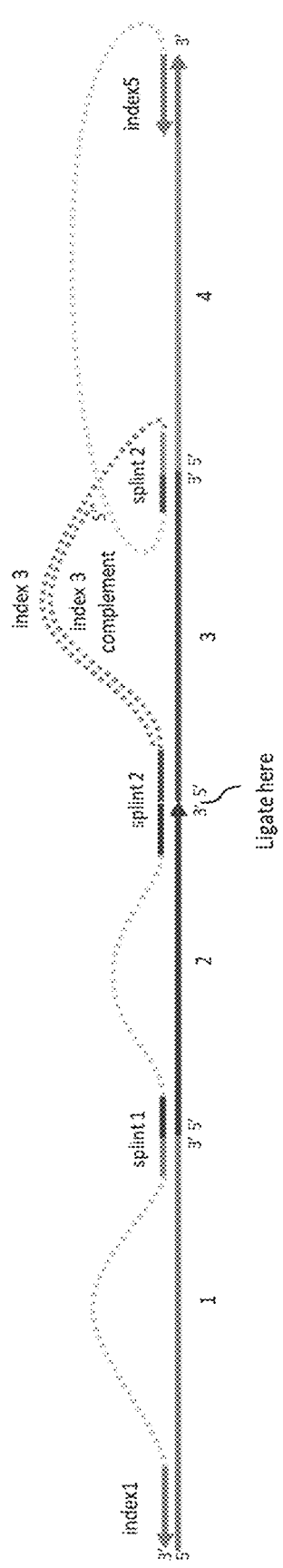
FIG. 9 depicts the second ligation step of a 4-part assembly process. The purified products of the restriction digestion (see (b) and (d) in FIG. 8) are then hybridized together as depicted in the schematic image (see Index3) and ligated to produce assembled product (1-2-3-4). This product can be purified, for instance by SPRI, and subject to additional ligation or amplified via PCR. For instance, primer sequences could be present between Index 1 and the assembly sequence of assembly component 1 (forward primer) and between Index5 and the assembly sequence of assembly component 4 (reverse primer).

In an aspect, the method is a 4-part assembly, as illustrated in FIGS. 7 to 9, where the assembly process is repeated on the ligation products of the first assembly. In this aspect, there are two ligation steps, separated by a restriction enzyme digestion step. The hybridization step forms two oligonucleotide structures as depicted in FIG. 7. In the top oligonucleotide structure depicted in FIG. 7, the oligonucleotide structure is in the orientation illustrated in FIG. 5B (but it can be designed in the orientation depicted in FIG. 5C). The indexed splint molecule comprises, 5' to 3', a first index sequence hybridized to the downstream assembly component 2 to form Index2, a splint sequence (splint 1), and a second index sequence hybridized to the upstream assembly component 1 to form Index1. Splint 1 is hybridized to the 3' terminal sequence of the upstream assembly component 1 and to the 5' terminal sequence of the downstream assembly component 2. In addition to the first splint structure (splint1), the indexed splint of the top oligonucleotide structure further comprises a second splint sequence (splint2) in the spacer section and another index sequence (to form Index3) between the 5' index sequence (Index2) and the first splint structure (splint1). The downstream assembly component 2 comprises a further structural feature, which is a restriction enzyme sequence 3' of the assembly sequence (depicted in FIG. 8).

In the bottom oligonucleotide structure depicted in FIG. 7, the oligonucleotide structure is in the orientation illustrated in FIG. 5C (but it can be designed in the orientation of FIG. 5B. The indexed splint molecule comprises, 5' to 3', a first index sequence hybridized to the upstream assembly component 3 to form Index4, a splint sequence (splint 3), and a second index sequence hybridized to the downstream assembly component 4 to form Index5. Splint 3 is hybridized to the 3' terminal sequence of the upstream assembly component 3 and to the 5' terminal sequence of the downstream assembly component 4. The indexed splint of the bottom oligonucleotide structure further comprises a complementary sequence of Index3 (Index3 complement) between the 5' index sequence (Index4) and splint 3.

The ligation step produces a ligation product of components 1 & 2, assembled product (1-2), and a second ligation product of components 3 & 4, assembled product (3-4) as illustrated in FIG. 8, structures (a) and (c), respectively. As illustrated in FIG. 8, the indexed splint of the top structure (a) comprises a restriction enzyme site (RE cutsite) 3' of the assembly sequence of assembly component 2 and 5' to index 2. The indexed splint of structure (c) comprises a restriction enzyme site 5' of the assembly sequence of assembly component 3, and 3' of index 3. The indexed splint comprises two further structural features: located between splint 2 and the index sequence for Index 4, the index sequence that is the complement sequence to form Index3, and a restriction enzyme site 5' of index sequence for Index 4. The ligation products are subject to type IIS restriction enzyme digestion to cleave the restriction enzyme sites in assembled product 1-2 and in assembled product 3-4 to remove Index2 and Index4 respectively. Consequently, the digestion product of ligation product 1-2 can be an upstream assembly component and the digestion product of ligation product 3-4 can be a downstream assembly component in another iteration of the method. The digestion products can be purified, e.g., by SPRI purification (e.g., SPRI stands for solid phase reversible immobilization), then subject to a hybridization step. The hybridization step produces the oligonucleotide structure illustrated in FIG. 9. As illustrated, double-stranded Index3 forms by hybridization of the Index3 sequences of the two indexed splint molecules. Splint 2 acts to hybridize to the assembly components to form the ligation site; the 5' element binds the 5' end of assembled product (3-4) and the 3' element binds the 3' end of assembled product (1-2). A second ligation step is performed, producing the multicomponent ligation product 1-2-3-4 (not shown). The product of the second ligation step can optionally be SPRI-purified and amplified via PCR.

As shown herein, index-based ligation where the hybridization of the opposite ends of two assembly components to a common indexed splint molecule with two complementary index sequences provides good specificity. For instance, the melting temperature (Tm) of the index elements may not be higher than the melting temperature (Tm) of each of the two hybridized splint elements. In this way, the index binding is stable under hybridization conditions, while the splint binding is metastable. Thus the specifically-designed index sequences can drive the hybridization reaction and avoid undesired binding between the splint sequence and unintended targets in the reaction mixture.

The same process can be repeated for assembly of even larger products.

It is further contemplated that there may be conditions wherein specificity might improve by a variation of the disclosed method. The following describes a method for increasing the melting temperature of the index sequences and thus increase specificity. This aspect also relies on a two-step ligation process. In brief, and as illustrated in FIGS. 10-13, in a first ligation step, the two assembly components oligos are hybridized to a molecule that comprises two index sequences adjacent to each other but does not comprise a splint region (see "index splint" in FIG. 10) and are ligated together at their indexing sequences, forming a much longer oligo in a first ligation step (see FIG. 11). After the first ligation step (ligating the ends of the index sequences), the temperature can be increased to above the melting temperature of the indexing sequences with their complementary splint sequence, and a second molecule ("construct splint" that hybridizes to two assembly targets) is added (see FIG. 12B) at this higher temperature allowing greater stringency lessening the chance of cross-hybridization between homologous constructs, and hence potentially even better specificity then the previously described embodiments. The second ligation event for each molecule occurs while the free ends of the ligation product of the first ligation hybridize with the splint oligos and are subsequently ligated to form a single-stranded loop (see FIG. 13). To stabilize the formation of the loop, one of the sections of the second splint may be substantially longer than the other section forming a stable duplex on one end while the other end only needs to come into contact briefly with the duplexed end in order for it to become ligated, forming the loop. Additionally, chimera formation can be inhibited by diluting the solution after the first ligation step by the addition of more buffer solution. This increases the probability of intra-molecular ligation and loop formation over intermolecular ligation by increasing the entropy of the solution.

Figure 10:
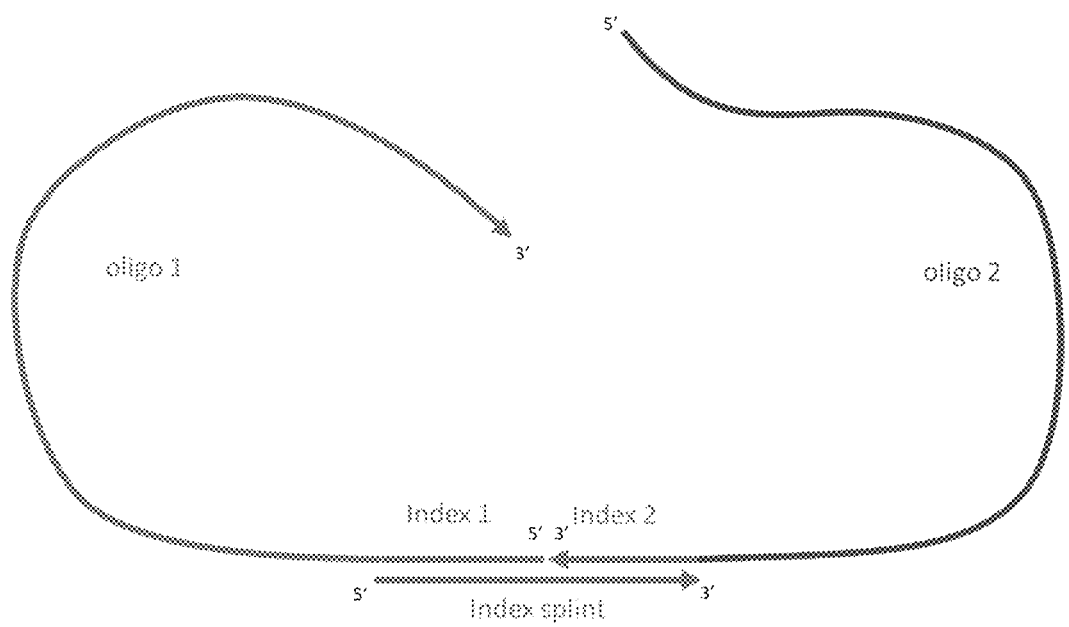
Figure 11:
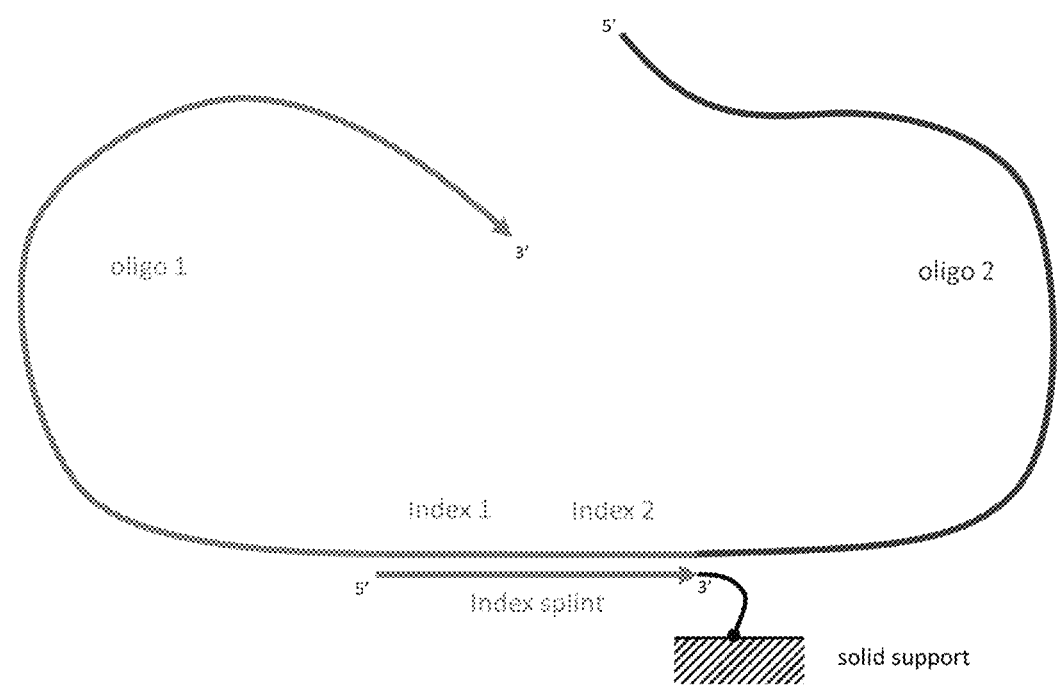

As illustrated in FIG. 10, the two assembly components are hybridized to a splint molecule by the index sequences at the 5' end of one assembly component and the index sequence at the 3' end of the other assembly component. After ligation, the ligation product comprises the two assembly components wherein the two index sequences are adjacent and ligated to each other, in the middle of the ligated product. See FIG. 11. After ligation, the ligation product remains hybridized by the now-ligated two index sequences (Index 1-Index 2) to the index splint and has a significantly increased melting temperature. For instance, in an aspect where each index sequence is 30 nucleotides long and each index element has a melting temperature of about 69° C. the combined melting temperature of the two index sequences in the duplex is about 17° C. higher to a mean temperature of about 86° C. This means that the temperature of the reaction solution can be raised to a temperature in the low 80s without denaturing the duplex.

Optionally, between the steps of the method, unbound fragments or un-ligated products can be removed from the reaction solution by, for instance, washing the hybridization solution away, to clean up the reaction solution. Optionally, this clean up can be performed by binding the indexing splint oligo to solid support. For example, the index splint oligo may have a biotin attached to either its 3' end (as shown in the FIG. 11) or at its 5'-end. The oligo duplexes can then be bound to magnetic streptavidin beads, commonly used for target enrichment. These need to be mixed in the tube, incubated for several minutes, then pulled to the side or bottom of the tube by means of a strong gradient magnetic field, as commonly performed with SPRI beads. Then, a wash step can be accomplished by withdrawing the hybridization solution, and refilling the container and rinsing the ligated products with a wash buffer in the tube once or multiple times. This will reduce the concentration of un-ligated oligonucleotides and reduce the likelihood of incorrect ligation events in the second ligation step.

The ligated product can be released from the duplex (and thus from the beads) by adding water or a more stringent ligation buffer, or by heating to above the melting temperature as appropriate for the buffer. A thermostable ligase, such as 9° N™ ligase (NEB, Ipswich, MA), can be added to the ligase buffer and the temperature increased to 80° C. or above, or to the highest temperature at which another thermostable ligase remains active, at which point the splint molecule for the free ends of the ligation product can added to the tube. Alternatively, the splint can be added to the mixture before heating and the ligase added after heating. This step can either be performed with the oligos in solution or while they remain bound to the magnetic beads. This second ligation event is depicted in FIGS. 12 and 13. After the period of the ligation reaction, the ligation reaction can be stopped by either by adding EDTA or simply by rapidly cooling to or at room temperature.

FIG. 13 shows optional additional structural features on the oligos, including, for instance, primer binding sites (PBS1 and BPS1), and an optional restriction enzyme site. Amplification can be performed either by PCR or by rolling circle amplification. Rolling circle amplification is performed by adding single primer complementary to either primer binding site on the looped oligo and a DNA polymerase with high processivity, such as bacteriophage phi29 DNA polymerase, to the tube. Alternatively, PCR can be performed by a polymerase, a pair of primers, and dNTPs, then thermally cycling in a thermal cycler.

Sometimes during PCR amplification of assembled products non-ligated oligonucleotides can be extended by the polymerase and create unwanted chimeras. The embodiments shown in FIGS. 12 and 13 that create circularized DNA can reduce this chimera production by the addition of an exonuclease step. In this additional step, an exonuclease can be used to digest single-stranded DNA and double-stranded from their 5' ends while leaving behind circular DNA assemblies. The exonuclease step should be carried out prior to PCT amplification. The digestion process can be stopped either by the addition of EDTA or by killing the enzyme by heating the reaction mixture to 75 C, or both. These circular constructs are subsequently amplified by PCR, or by rolling circle amplification using a processive polymerase, such as phi29.

In an aspect, the first ligation step to ligate the two assembly components in FIG. 10 is omitted. The second splint ("construct splint") hybridizes to construct sequence at the 5' and 3' free ends of the two assembly components, which are then ligated.

Figure 12A:
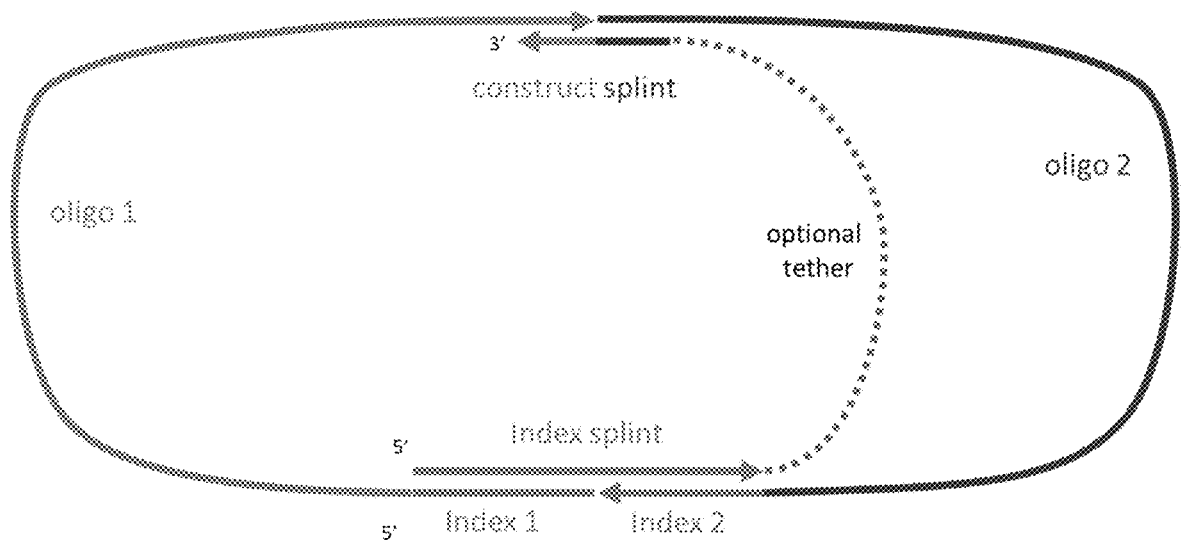
FIGS. 12A and 12B depict an oligonucleotide structure wherein a second splint molecule ("construct splint) is hybridized to the 3' and 5' ends of the assembly component.
Figure 12B:
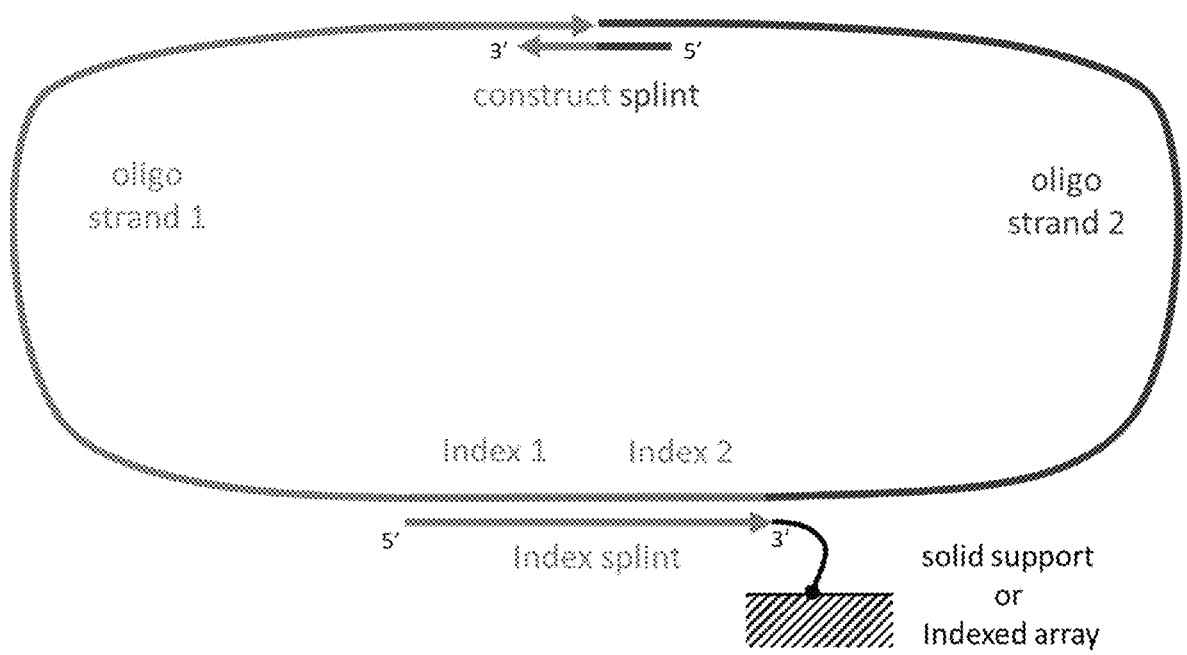
Figure 13:
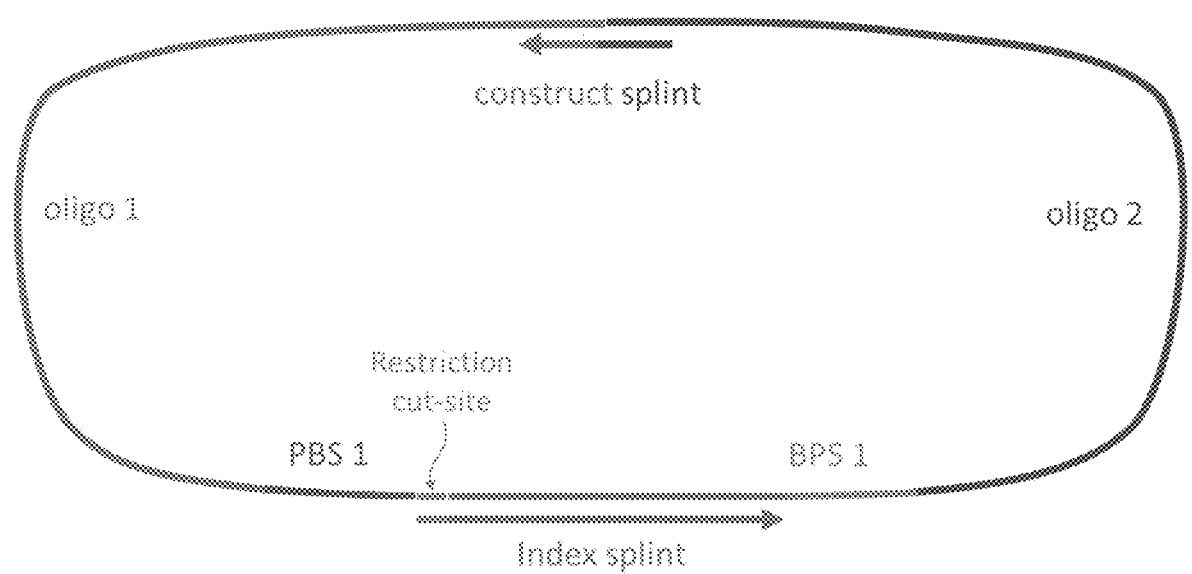

In another embodiment related to FIGS. 10-13, the index splint and the construct splint are connected by means of a linker molecule or sequence ("optional tether" in FIG. 12A). The molecule has components of the indexed splint of FIG. 5A but in a different 5' to 3' order.

In some embodiments of the present disclosure, the multicomponent construct can be first assembled in solution according to the present disclosure, and attached to a solid substrate post-assembly by any method known in the art. Thus, the present disclosure can be used to prepare arrays of multicomponent constructs wherein the multicomponent constructs are attached to the array substrate post-assembly. Subsequently, the multicomponent constructs or a pool or a plurality of pools of the multicomponent constructs can optionally and selectively be cleaved from the array substrate and be used as a library or libraries. Alternatively, the multicomponent construct may be attached to beads. The constructs may be attached to the beads through chemical means, or by specific hybridization. Depending on the method of attachment, different beads may be used to capture specific different constructs, or one bead may capture multiple constructs. Attachment of the library to beads may provide advantages for storing, washing, concentrating, or enzymatically manipulating the libraries.

Kits

The present disclosure also provides kits useful for carrying out the disclosed method. In one aspect, kits containing reagents for performing the above-described methods are provided, including an oligonucleotide library comprising a mixture of single-stranded oligonucleotides comprising at least one type of upstream assembly component, one type of downstream assembly component, and an indexed splint for directing ligation of the assembly components, and a DNA ligase. In certain embodiments, the kit includes one or more other reaction components. In certain embodiments, an appropriate amount of one or more reaction components is provided in one or more containers or held on a substrate. Examples of additional components of the kits include, but are not limited to, reaction buffers, one or more reagents (e.g., probes or PCR primers) for detecting ligation products and the like. The reaction components used can be provided in a variety of forms. For example, the components (e.g., enzymes, oligonucleotides, probes and/or primers) can be suspended in an aqueous solution or bound to a bead or as a freeze-dried or lyophilized powder or pellet. The kits of the disclosure can be provided at any suitable temperature. For example, for storage of kits containing protein components or complexes thereof in a liquid, it is preferred that they are provided and maintained below 0° C., preferably at about −20° C., possibly in a freeze-resistant solution containing glycerol or other suitable antifreeze.

A kit or system may contain, in an amount sufficient for at least one assay, any combination of the components described herein. In some applications, one or more reaction components may be provided in pre-measured single use amounts in individual, typically disposable, tubes or equivalent containers. The amount of a component supplied in the kit can be any appropriate amount and may depend on the market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

The disclosed method of assembly relies on a stable and specific hybridization between the index sequences of the indexed splint molecule and assembly component molecules. In contrast, prior art methods utilizing splints to direct assembly rely on a stable and specific hybridization between the splint molecule and the two assembly components. It is believed, without being held to theory, that a fundamental differentiation between the approach of the present disclosure (FIGS. 5A-5C) from prior art approaches is that the desired assembly sequence is not used to bring the pieces to be assembled into position for ligation in the disclosed method. The splint sequence in the disclosed method of assembly is designed to be too short to be a stable hybridization and thus is not sufficient to allow assembly absent index hybridization. The index sequences of the indexed splint molecule are not part of the construct sequence and thus are not affected by homology between library members. This is an unexpected benefit and improvement over previous high-throughput methods of multiplex assemblies.

EXAMPLES

Aspects of the present teachings can be further understood in light of the following examples, which should not be construed as limiting the scope of the present teachings in any way.

Example 1

The following experiment was designed and performed to evaluate preparing a low-homology library in solution using the oligonucleotide splint structures depicted in FIGS. 1, 2, and 3. Thus, there were three types of test splint molecules evaluated. The term "test splint molecule" refers to the single splint molecule in FIG. 1. In FIGS. 2 and 3, "test splint molecule" refers to the two oligonucleotide structure formed by the hybridization of the complementary index sequences to form the index element. The index element in FIGS. 2 and 3 was the same, and had Tms in the range of 60° C. to 75° C. The high Tm of the hybridized index effectively makes the two nucleotide structure a single molecule at temperatures below the Tm.

Construct sequences were taken from a set of low-homology genomic sequences, UTRs (untranslated regions). One hundred forty (140) UTRs were assembled. By design of the splint molecules tested, a correct construct was a UTR sequence ligated to the same UTR sequence. Thus, for the 140 different UTRs, there were 140 different test splint molecules and 140 total correct constructs possible to assemble, and 19,460 total incorrect constructs possible. Typically, each of the 140 UTRs have two versions in the original oligo library: one version has a primer site at the 5' end and another version has a primer site at the 3' end for the PCR amplification and introducing the required adaptor for MiSeq (Illumina).

Three ratios (1:1, 2:1, and 4:1) of test splint molecule-to-construct were tested for each type of test splint molecule. For the test splint molecules of FIGS. 2 and 3 (both of which have an index), a +/−3 nucleotide spacer (referred to as a stilt) was also tested. The 3 nucleotide stilt was located between the index and splint portions of the test splint molecule. As a result, there were fifteen sets assembled in this experiment. Each set had 140 correct UTR constructs that could be assembled from the 420 different UTR sequences. Products from the different sets were distinguishable by sequencing, where different sequences were printed different molecular copy numbers for each subset in the production of DNA library material.

For each set, an oligo library was prepared of the UTRs and the test splint molecule. About 80 ng of the library was solubilized (in a buffer suitable for both the kinase reaction and the ligase reaction) and then subjected to a kinase reaction using T4 polynucleotide kinase (NEB) according to manufacturers' recommendations, in order to phosphorylate the 5' terminus of the DNA oligos. The kinased products were hybridized by incubation in a water bath cooling from 93° C. to 44° C. over 1.75 hours to form the oligonucleotide structures depicted in FIGS. 1, 2, and 3. Hybridized products were then heated to the ligation temperature and 1 microliter (µl) 9° N™ ligase (New England Biolabs Inc., Ipswich, MA) was added. The ligation reaction proceeded for 1 hour. The ligated products were purified using 1.5× AMPure® XP beads (Beckman Coulter, Brea, CA) and amplified by PCR. The PCR products were sequenced by NGS (next-generation sequencing) to characterize the extent of correct assembly in each set.

Results

Figure 14:
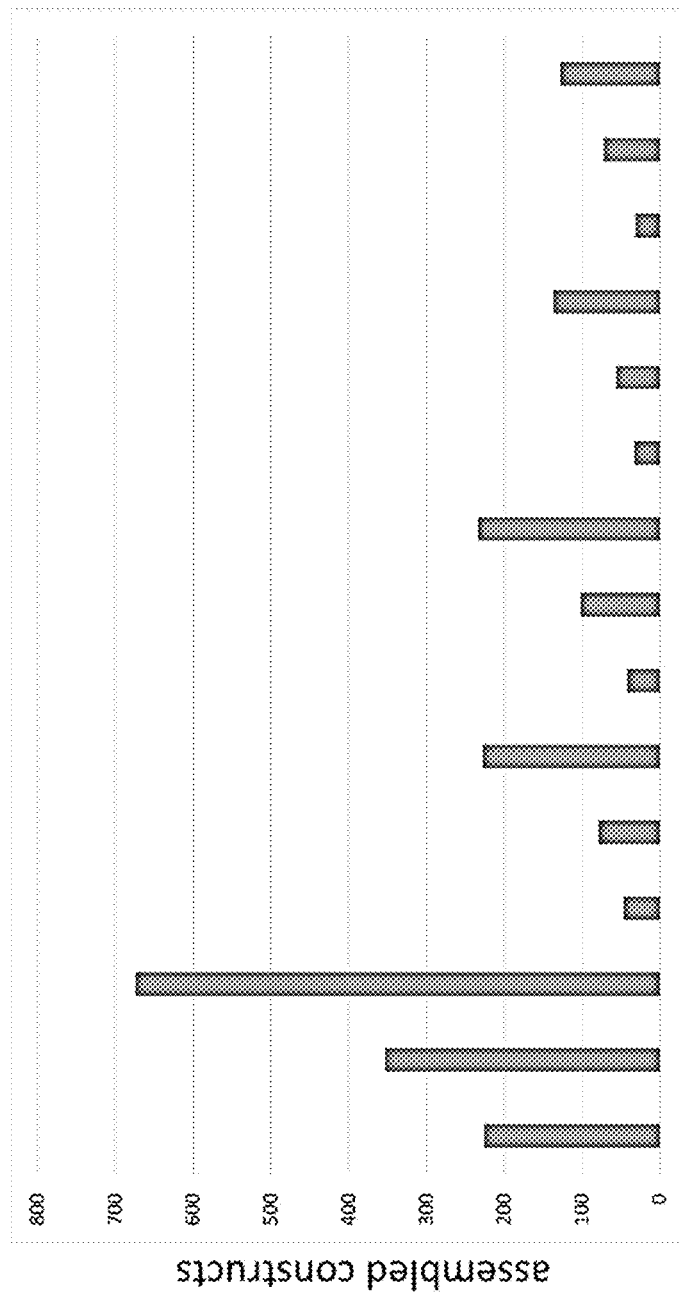
FIG. 14 depicts a graph of data for an experiment evaluating solution assembly of a low-homology library using three types of test splint molecules as depicted in the oligonucleotide structures (which each further include an assembly component 1 and assembly component 2) illustrated in FIGS. 1, 2 and 3. Three ratios of splint-to-construct were tested (1:1, 2:1 and 4:1) for each type of test splint molecule. The test splint molecules of FIGS. 2 and 3 were prepared with (+) and without (−) a 3 nucleotide (nt) stilt. Assembled constructs were characterized by next-generation sequencing (NGS) of PCR-amplified assembled constructs. The Y-axis in the graph is the average number of reads for correctly assembled constructs in each of the 15 sets. See Example 1 for more information.

The NGS read data are shown in FIG. 14. The data show that all three types of test splint molecules (of the oligonucleotide structures depicted in FIG. 1, 2 or 3) worked in all 15 sets. The test splint molecule of FIG. 1 worked the best. In particular, the set wherein the splint/construct molecular ratio was 4:1 worked best of the three ratios tested, having close to 700 average number of reads for correctly assembled constructs. The data for FIGS. 2 and 3 are similar to each other, with the FIG. 2 data showing slightly higher average number of reads for correctly assembled constructs. The presence of the 3 nucleotide stilt in the FIG. 2 test splint molecule had little impact on the FIG. 2 test splint molecule. The presence of the 3 nucleotide stilt in the FIG. 3 test splint molecule resulted in a slightly reduced average number of reads relative to the data for the test splint molecule without the stilt.

Example 2

To examine a different test splint molecule from those in Example 1, the following experiment was designed and performed. This experiment used a test splint molecule as illustrated in the oligonucleotide structure of FIG. 5B. The test splint molecule is an indexed splint molecule, which is a single oligonucleotide sequence that contains index sequences located at the 5' and 3' termini of the test splint molecule and that flank the splint region that binds to the two assembly components. The assembly components (comprising the assembly sequences to be ligated to form an assembled construct) were prepared to further include reverse complement sequences to the index sequences of the test splint molecule and thereby to enable hybridization of the test splint molecule to an assembly component at two locations. For the left assembly component, the test splint molecule binds: (1) at the splint element that binds to a specific sequence at the 3' end of a left assembly component and (2) at the index sequence at the 5' terminus of a left assembly component (hybridizing to form an index element). For the right assembly component, the test splint molecule binds (1) at the splint element that binds to a specific sequence at the 5' end of a right assembly component and (2) at the index sequence at the 5' end of a right assembly component (hybridizing to form another index element). The index element at the 3' terminus of the left assembly component has a different sequence than index element at the 3' terminus of the right assembly component so there is no cross-hybridization between the two separate index elements. The index element at the 5' terminus of the left assembly component consists of 30 nucleotides and has a Tm in the range of 65-72° C., and the index element at the 3' terminus of the right assembly component consists of 30 nucleotides and has a Tm in the range of 65-72° C.

Figure 15:
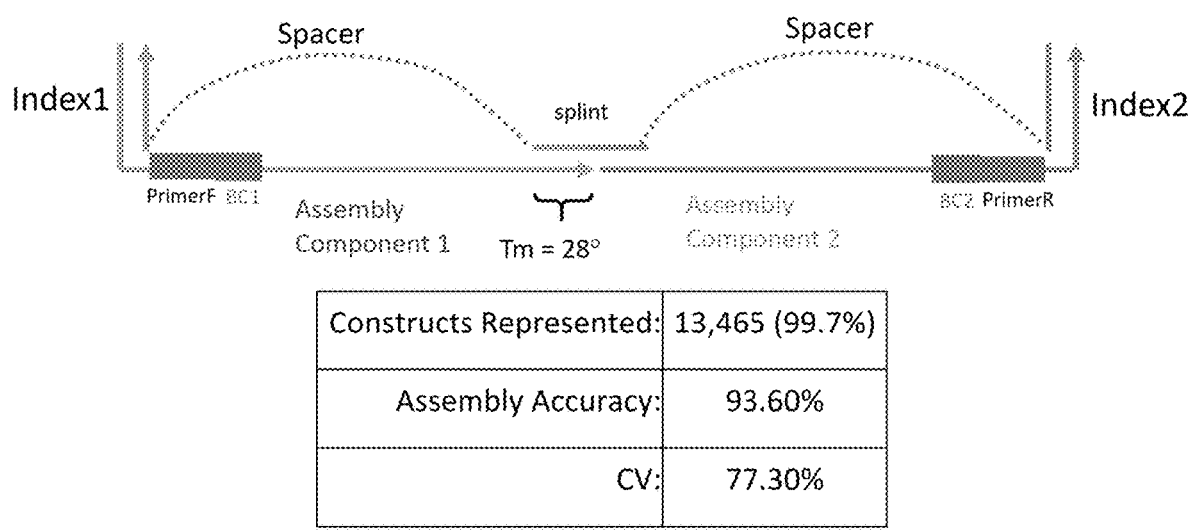
FIG. 15 depicts a schematic of a test splint molecule of FIG. 5B (top panel) and data from a proof of concept experiment (bottom panel). The arrow heads indicate the 3' end of the oligonucleotides; the flat ends are the 5' end of the oligonucleotides. PrimerF-location for a forward primer for PCR. PrimerR-location for a reverse primer for PCR. Tm is melting temperature of each section of the splint hybridized (i.e., the melting temperature of the 5' element and of the 3' element) to the left and right construct oligonucleotides (respectively assembly component 1 and assembly component 2). BC1 and BC2 indicate the position of paired barcode sequences. Index1 and Index2 indicate the index elements in the oligonucleotide structure. The dotted lines between the index sequences and the splint sequence of the indexed splint molecule indicate spacer sequences, which in this test is a 20-base polyT nucleotide sequence. See Example 2 for more information.

Construct sequences (2250 sequences) were taken from a set of low-homology genomic sequences, UTRs (untranslated regions). The assembly sequences were 200 nucleotides in length. Assembly components comprised a UTR construct sequence, an index sequence, a barcode and a primer sequence. As illustrated in FIG. 15, the left assembly component (Left) comprised, 5' to 3', an index sequence (to form Index 1 when hybridized to an indexed splint), a primer sequence (PrimerF), a barcode (BC1), and the assembly sequence. The right assembly component (Right) comprised, 5' to 3', the assembly sequence, a barcode (BC2), a primer sequence (PrimerR) and an index sequence (to form Index 2 when hybridized to an indexed splint).

The test splint molecules comprised, 5' to 3', an index sequence (hybridizes to a right assembly component to form index 2 in the oligonucleotide structure), a spacer (dotted line), a splint sequence, another spacer (dotted line), and another index sequence (hybridizes to form index 1 in the oligonucleotide structure). The splint sequence contains a 5' sequence element the hybridizes to the 5' terminal sequence of the assembly sequence of the right assembly component, and a 3' sequence that hybridizes to the 3' terminal sequence of the assembly sequence of the right assembly component. Each of the 5' sequence element and the 3' sequence element of the splint is at least 12 nucleotides long and each has a Tm of greater than or equal to 28° C. (as calculated using EQ. 1: $Tm=(2*(A_{count}+T_{count}))+(4*(C_{count}+G_{count}))-7$).

By design of the splint molecules utilized in the experiment, a correct construct was a UTR ligated to the same UTR, yielding a 400 nucleotide multicomponent construct (not including the non-construct sequences). Each UTR assembly component was designed to further comprise 6 unique barcode pairs. A correct construct is indicated by the left and right barcodes being correctly paired in the assembled construct. Thus, for each UTR, there are six correct constructs possible (and 30 incorrect constructs possible). Since 2250 different UTR sequences were tested and 6 unique barcode pairs, there are a total of 13,500 unique indexed splint molecules (2250×6), and 13,500 unique correct constructs possible.

An oligo library was prepared containing the UTR component constructions and the indexed splint molecules. About 80 ng of the library was solubilized and then subjected to a kinase reaction using T4 polynucleotide kinase (NEB) according to manufacturers' recommendations, in order to phosphorylate the 5' terminus of the DNA oligos. The kinased products were hybridized by incubation in a water bath cooling from 93° C. to 44° C. over 1.75 hours. Hybridized products were then heated to the ligation temperature 60.6° C. and 1 microliter (μl) 9° N™ ligase (New England Biolabs Inc., Ipswich, MA) was added. The ligation reaction proceeded for 10 minutes. The ligated products were purified using 1.5× AMPure® XP beads (Beckman Coulter, Brea, CA) and amplified by PCR. The PCR products were sequenced by NGS (next-generation sequencing) to characterize the extent of correct assembly.

Results

The data are shown in the table in FIG. 15. Of the 13,500 possible correct constructions, 13,465 were detected by sequencing the library with fewer than 10,000,000 reads. Based on unique barcodes located at opposite ends of the assemblies, this data shows 99.70% of the possible correct constructions were assembled in the reaction, but does not indicate the full-length sequence accuracy of each sequence between the barcodes.

Thus, the FIG. 5B oligonucleotide structure enabled a notably high number of correct constructs. This is a very consequential number for the preparation of oligonucleotide library.

Example 3

The following experiment was designed and performed to test assembly using the oligonucleotide structures of FIGS. 1, 2, and 5B. The experiment was designed to compare three (3) types of oligonucleotide libraries: (a) a complex library, (b) a tiled library, and (c) a homologous library. The 3 types of libraries are schematically depicted in FIG. 16.

In the complex library for this experiment, the sequences have little sequence similarity, except the peripheral primer sites. The complex library (type a) had 600 distinct UTR sequences (i.e., total of 600 possible correct assembled constructs). The homologous library (type c) utilized 60 distinct UTR sequences and each distinct UTR sequence had 10 uniquely barcoded constructs (total of 600 possible correct assembled constructs). In the tiled library for this experiment, each member overlaps sequence identity with 3 other members. For the tiled library (type b), there were 4 tiled constructs (with overlap sequence identity of 82-246 base pairs) for each of 150 distinct UTR sequences (total I of 600 possible correct assembled constructs). For each library, the assembled constructs were 400 bases long.

Each type of library was tested with each type of test splint molecule (see the oligonucleotide structures of FIGS. 1, 2, and 5B), resulting in 9 categories tested as shown in Table 1.

TABLE 1

| Category | Indexed Splint | Library type |
| --- | --- | --- |
| 1a | FIG. 1 | complex library (type a) |
| 1b |  | tiled library (type b) |
| 1c |  | The homologous library (type c) |
| 2a | FIG. 2 | complex library (type a) |
| 2b |  | tiled library (type b) |
| 2c |  | The homologous library (type c) |
| 3a | FIG. 5B | complex library (type a) |
| 3b |  | tiled library (type b) |
| 3c |  | The homologous library (type c) |

The nine categories were all in the same library and assembled together. The PCR products were sequenced by NGS (next-generation sequencing) to characterize the extent of correct assembly.

Results

Figure 17:
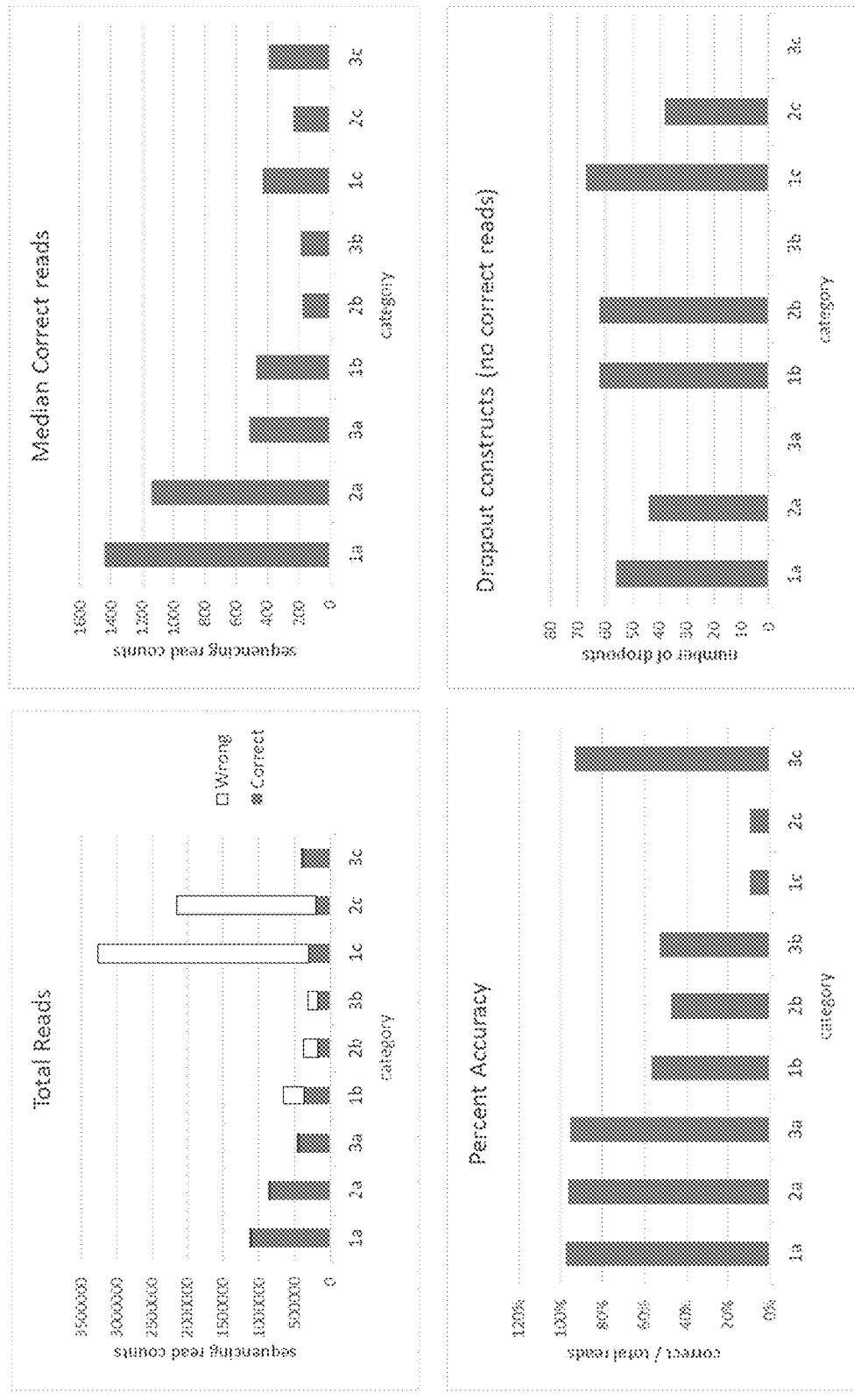
FIG. 17 depicts representative data for testing assembly utilizing three types of test splint molecule (see the oligonucleotide structures of FIGS. 1, 2, and 5B) in three types of representative oligo libraries (see FIG. 16). See Example 3 for more information.

The data are shown in FIG. 17. The data for the total number of reads, correct and incorrect) are depicted in the upper left graph. These data show that the indexed splint of FIG. 1 and FIG. 2 in the homology library (type c) resulted in a large majority of incorrectly assembled constructs. The percent accuracy data (i.e., total number of correct reads relative to the total number of reads) are depicted in the lower left graph. All three types of indexed splint molecules yielded high accuracy in the complex library (type a) and moderate level of accuracy in the tiled library (type b). Only the splint molecule of FIG. 5B had a high accuracy for the homologous library (type c). The median correct reads data are depicted in the upper right graph. The data for number of dropout constructs is depicted in the lower right graph. A "dropout construct" refers to a correct construct for which there are no correct reads (there are 600 possible correct constructs in for each library). These data show that the indexed splint of FIG. 1 and FIG. 2 assembly had dropout constructs for each type of library. For instance, the FIG. 1 indexed splint showed over 50 dropout constructs for the complex library (type a), over 60 dropout constructs for the tiled library (type b) and close to 70 dropout constructs for the homologous library (type c). There were no dropout constructs for any of libraries for the FIG. 5B indexed splint.

Two notable aspects for the FIG. 5B data are observed in this data. First, the assembly method using the FIG. 5B indexed splint molecule was the only one that could assemble the type c (complex library) library type with a useful level of accuracy (see lower left graph). Second, the assembly method using the FIG. 5B indexed splint molecule had no dropouts (see lower right graph). All 600 of the possible correct assembled constructs were assembled in the FIG. 5B assembly. In contrast, the other two approaches had 50-80 dropouts, i.e., constructs not constructed of the 600 possible correct constructs.

These data are indicative of the effect on correct assembly using the indexed splint molecule depicted in the FIG. 5B, and demonstrates correct assembly of constructs that would otherwise be impossible due to promiscuous hybridization of the splint molecule.

Example 4

The following experiment was designed and performed to measure the effect of two experimental variables in assembling constructs utilizing the indexed splint molecule as shown in the FIG. 5B.

Figure 18:
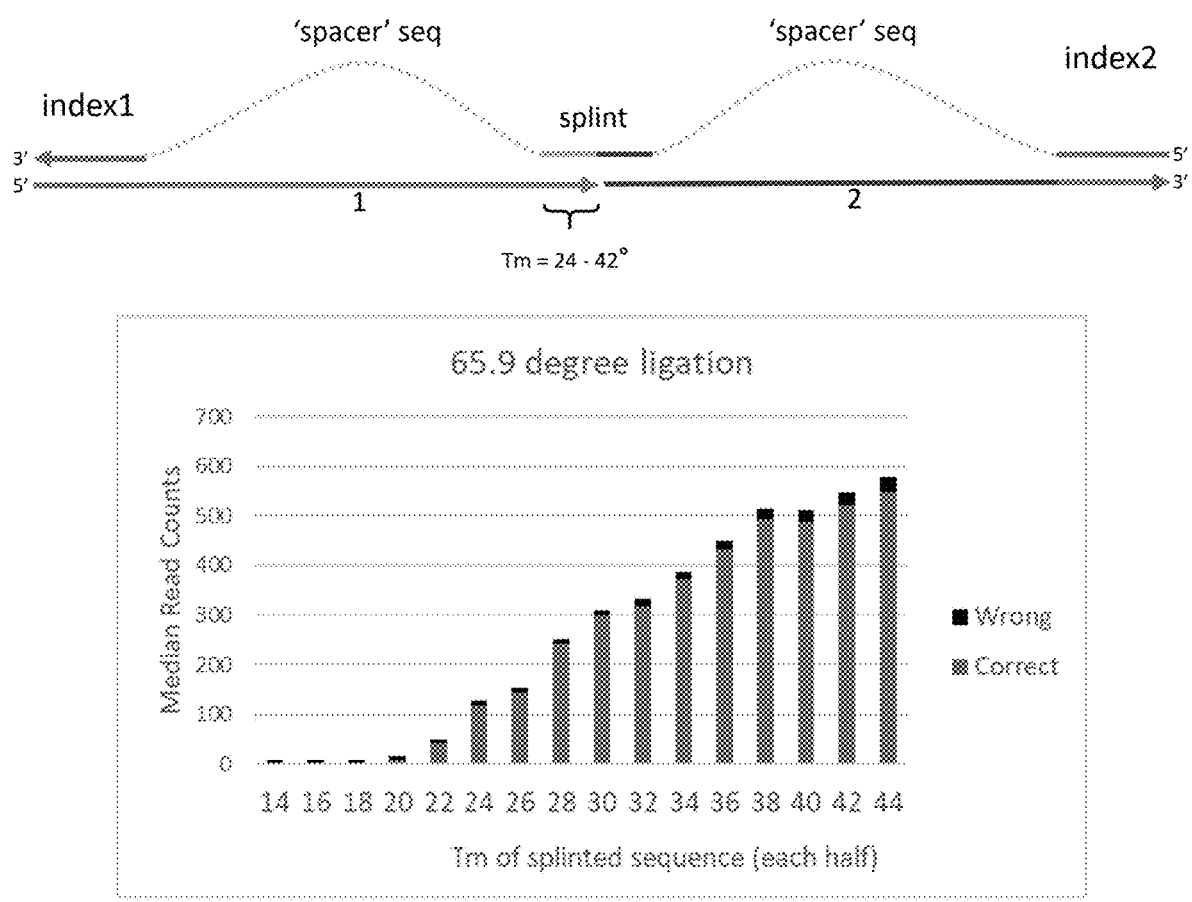
FIG. 18 depicts a schematic of test splint molecule (oligonucleotide structure of FIG. 5B) and representative data for assembly using the same with different splint lengths and ligation temperature. In the experiment, a range of melting temperatures (Tm) for each of the splint-to-construct hybridized elements (5' element and 3' element) was designed, and ligation at eight (8) different temperatures was tested. The data for the number of median read counts for the 65.9° C. ligation data is depicted in the graph. For each splint temperature, the fraction of correct reads and wrong reads is represented in the median read counts. See Example 4 for more information.

Construct sequences were taken from a set of low-homology genomic sequences, UTRs (untranslated regions). Sixteen (16) variable lengths for each half of the splinted sequence, organized by melting temperature (Tm as calculated by $Tm=(2*(A_{count}+T_{count}))+(4*(C_{count}+G_{count}))-7$) were designed. Temperature thresholds from 14° C. to 44° C. in 2° C. were prepared for the splint halves. Forty (40) UTR unique sequences were assembled for each splint design (16×40=640 UTR sequences total). Ten (10) unique barcodes were used for each of the UTR sequence (total of 6,400 possible correct constructs). A 'correct' pair was called if the barcodes were correctly paired in the assembled construct (measured by NGS). Assembly components further comprised sequences for forward primer (upstream assembly component) and reverse primer (downstream assembly component) to permit PCT amplification. Libraries were assembled at 8 different ligation temperatures. FIG. 18 depicts a schematic of the FIG. 5B test splint molecule for this experiment.

An oligo library was prepared of the UTR assembly components and the various test splint molecule. About 80 ng of the library was solubilized (in a buffer suitable for both the kinase reaction and the ligase reaction) and then subjected to a kinase reaction using T4 polynucleotide kinase (NEB) according to manufacturers' recommendations, in order to phosphorylate the 5' terminus of the DNA oligos. The kinased products were hybridized by incubation in a water bath cooling from 93° C. to 44° C. over 1.75 hours to form the oligonucleotide structure depicted in the FIG. 5B. Hybridized products were then heated to one of the ligation temperatures tested and 1 microliter (μl) 9° N™ ligase (New England Biolabs Inc., Ipswich, MA) was added. The ligation reaction proceeded for 1 hour. The ligated products were purified using 1.5× AMPure® XP beads (Beckman Coulter, Brea, CA) and amplified by PCR. The PCR products were sequenced by NGS (next-generation sequencing) to characterize the extent of correct assembly.

Results

The data generally demonstrate that the specificity of assembly increases at higher ligation temperatures. The data also generally demonstrate that the efficiency of assembly constructs with shorted splinted lengths (lower Tm) decreases at high ligation temperatures. Representative data is depicted the graph in FIG. 18. The data illustrate the high extent of correct assembly possible utilizing indexed splint molecule in the FIG. 5B, over a range of Tm's for the two splint segments.

EXEMPLARY EMBODIMENTS

Products

Embodiment 1. An oligonucleotide structure for assembling two nucleic acid components to produce a multicomponent ligation product, the oligonucleotide structure comprising a first single-stranded oligonucleotide, a second single-stranded oligonucleotide and an indexed splint, wherein the first single-stranded oligonucleotide and the second single-stranded oligonucleotide are hybridized in part to the indexed splint.

Embodiment 2. The oligonucleotide structure of Embodiment 1, wherein
(a) the indexed splint comprises a splint sequence, and a first index sequence and a second index sequence flanking the splint sequence;
(b) the splint sequence is hybridized to both the 3' end of the first single-stranded oligonucleotide and the 5' end of the second single-stranded oligonucleotide; and
(c) the first index sequence is hybridized to the 5' end of the first single-stranded oligonucleotide to form a first double-stranded index element, and the second index sequence is hybridized to the 3' end of the second single-stranded oligonucleotide to form a second double-stranded index element.

Embodiment 3. The oligonucleotide structure Embodiment 2, wherein the splint sequence of the indexed splint contains:
(a) a 5' element that is hybridized to (is a reverse complement to) the 5' end of the second single-stranded oligonucleotide, and
(b) a 3' element that is hybridized to (is a reverse complement to) the 3' end of the first single-stranded oligonucleotide,
wherein the 5' element and the 3' element of the splint sequence are contiguous, i.e., without intervening nucleotides.

Embodiment 4. The oligonucleotide structure of Embodiment 3, wherein each of the 5' hybridized splint element of (a) and the 3' hybridized splint element of (b) has a melting temperature (Tm) from about 14° C. to about 44° C., wherein $$Tm=(2*(A_{count}+T_{count}))+(4*(C_{count}+G_{count}))-7.$$

Embodiment 5. The oligonucleotide structure of any one of Embodiments 2, 3 and 4, wherein:
(1) the first index sequence is located at the 3' end of the indexed splint; and
(2) the second index sequence is located at the 5' end of the indexed sequence.

Embodiment 6. The oligonucleotide structure of Embodiment 5, wherein:
(a) the first single-stranded oligonucleotide comprises from 5' to 3':
(1) a third index sequence comprising the 5' terminal sequence of the first single-stranded oligonucleotide (left assembly component), and
(2) the first DNA sequence component to be ligated into the multicomponent ligation product, the first DNA sequence component comprising the 3' terminal sequence of the first single-stranded oligonucleotide (left assembly component); and
(b) the second single-stranded oligonucleotide comprises from 5' to 3':
(1) the second DNA sequence component to be ligated into the multicomponent ligation product comprising the 5' terminal sequence of the second single-stranded oligonucleotide and
(2) a fourth index sequence comprising 3' terminal sequence of the second single-stranded oligonucleotide; and
(c) the indexed splint comprises from 5' to 3':
(1) a 5' terminal sequence which is the second index sequence,
(2) an optional first spacer sequence,
(3) the splint sequence,
wherein the 5' element of the splint sequence hybridizes to (is the reverse complement of) the 5' terminal sequence the second single-stranded oligonucleotide, and
wherein the 3' element of the splint sequence hybridizes to (is the reverse complement of) the 3' terminal sequence of the first single-stranded oligonucleotide, and
(4) an optional second spacer sequence, and
(5) a 3' terminal sequence which is the first index sequence.

Embodiment 7. The oligonucleotide structure of Embodiment 6, wherein each spacer sequence independently consists of 1 to 30 nucleotides.

Embodiment 8. The oligonucleotide structure of any one of Embodiments 2, 3 and 4, wherein:
(1) the first index sequence is located at the 5' end of the indexed splint; and
(2) the second index sequence is located at the 3' end of the indexed sequence.

Embodiment 9. The oligonucleotide structure of Embodiment 8, wherein:
(a) the first single-stranded oligonucleotide comprises from 5' to 3':
(1) a third index sequence comprising the 5' terminal sequence of the first single-stranded oligonucleotide, and
(2) the first DNA sequence component to be ligated into the multicomponent ligation product, the first DNA sequence component comprising the 3' terminal sequence of the first single-stranded oligonucleotide (left assembly component); and
(b) the second single-stranded oligonucleotide comprises from 5' to 3':
(1) the second DNA sequence component to be ligated into the multicomponent ligation product comprising the 5' terminal sequence of the second single-stranded oligonucleotide and
(2) a fourth index sequence comprising 3' terminal sequence of the second single-stranded oligonucleotide; and; and
(c) the indexed splint comprises from 5' to 3':
(1) a 5' terminal sequence which is the first index sequence,
(2) an optional first spacer sequence,
(3) the splint sequence,
wherein the 5' element of the splint sequence is hybridized to (is the reverse complement of) the 5' terminal sequence of the second single-stranded oligonucleotide, and
wherein the 3' element of the splint sequence is hybridized to (is the reverse complement of) the 3' terminal sequence of the first single-stranded oligonucleotide (left assembly component, and
(4) an optional second spacer sequence, and
(5) a 3' terminal sequence which is the second index sequence.

Embodiment 10. The oligonucleotide structure of Embodiment 8 or 9, wherein each spacer sequence independently consists of 1 to 30 nucleotides.

Embodiment 11. The oligonucleotide structure of any one of Embodiments 2 to 10, wherein each double-stranded index element comprises 10 to 40 basepairs.

Embodiment 12. The oligonucleotide structure of any one of Embodiments 2 to 11, wherein each double-stranded index element has a melting temperature (Tm) from about 10° C. to about 80° C., wherein $$Tm=(2*(A_{count}+T_{count}))+(4*(C_{count}+G_{count}))-7.$$

Embodiment 13. The oligonucleotide structure of any one of Embodiments 6, 7, 9, 10 and 11, wherein the fourth index sequence (Segment F) is removably (or detachably) linked to the second DNA sequence component.

Embodiment 14. The oligonucleotide structure of Embodiment 13, wherein the second single-stranded oligonucleotide further comprises a Type II restriction enzyme site 3' to second DNA sequence component, wherein the restriction enzyme site of cleavage is immediately 3' of the second DNA sequence component.

Embodiment 15. The oligonucleotide structure of Embodiment 13, wherein the second single-stranded oligonucleotide is removably (or detachably) linked to the second DNA sequence component by a cleavable linker, wherein the site of cleavage is immediately 3' of the second DNA sequence component.

Embodiment 16. The oligonucleotide structure of any one of Embodiments 2 to 15, further comprising a least one blocking oligonucleotide component that is hybridized to (a reverse complement to) a sequence segment of Segment D or Segment E, wherein the sequence segment excludes the sequence hybridized to the splint.

Embodiment 17. A set or library of oligonucleotide structures of any one of Embodiments 1 to 16.

Embodiment 18. A kit comprising the set or library of Embodiment 17.

Embodiment 19. The kit of Embodiment 18 further comprising a DNA ligase.

Methods

Embodiment 20. A method for assembling two nucleic acid components to produce a multicomponent ligation product, comprising;
(A) hybridizing a first single-stranded oligonucleotide comprising a first DNA sequence component and a second single-stranded oligonucleotide comprising a second DNA sequence component to an indexed splint, wherein both the 5' end and the 3' end of the first single-stranded oligonucleotide are hybridized to the indexed splint and both the 5' end and the 3' end of the second single-stranded oligonucleotide are hybridized to the indexed splint; and
(B) ligating the 3' end of the first single-stranded oligonucleotide to the 5' end of the second single-stranded oligonucleotide, thereby producing a first multicomponent ligation product.

Embodiment 21. The method of Embodiment 20, wherein:
(a) the indexed splint further comprises a splint sequence, and a first index sequence and a second index sequence flanking the splint sequence;
(b) the splint sequence hybridizes to both the 3' end of the first single-stranded oligonucleotide and the 5' end of the second single-stranded oligonucleotide; and
(c) the first index sequence hybridizes to the 5' end of the first single-stranded oligonucleotide to form a first double-stranded index element, and the second index sequence hybridizes to the 3' end of the second single-stranded oligonucleotide to form a second double-stranded index element.

Embodiment 22. The method of Embodiment 21, wherein the splint sequence of the indexed splint contains:
(a) a 5' element that hybridizes to the 5' end of the second single-stranded oligonucleotide forming a double-stranded 5' splint element, and
(b) a 3' element that hybridizes to the 3' end of the first single-stranded oligonucleotide forming a double-stranded 3' splint element, wherein the 5' element and the 3' element of the splint sequence are contiguous, i.e., without intervening nucleotides.

Embodiment 23. The method of Embodiment 22, wherein the double-stranded 5' splint element and the double-stranded 3' splint element each has a melting temperature (Tm) from about 10° C. to about 80° C., wherein $$Tm=(2*(A_{count}+T_{count}))+(4*(C_{count}+G_{count}))-7.$$

Embodiment 24. The method of Embodiment 21, 22 or 23, wherein:
(1) the first index sequence is located at the 3' end of the indexed splint; and
(2) the second index sequence is located at the 5' end of the indexed splint.

Embodiment 25. The method of Embodiment 24, wherein:
(a) the first single-stranded oligonucleotide comprises from 5' to 3':
(1) a third index sequence comprising the 5' terminal sequence of the first single-stranded oligonucleotide, and
(2) the first DNA sequence component to be ligated into the multicomponent ligation product, the first DNA sequence component comprising the 3' terminal sequence of the first single-stranded oligonucleotide; and
(b) the second single-stranded oligonucleotide comprises from 5' to 3':
(1) the second DNA sequence component to be ligated into the multicomponent ligation product comprising the 5' terminal sequence of the second single-stranded oligonucleotide and
(2) a fourth index sequence comprising 3' terminal sequence of the second single-stranded oligonucleotide; and
(c) the indexed splint comprises from 5' to 3':
(1) a 5' terminal sequence which is the second index sequence,
(2) an optional first spacer sequence,
(3) the splint sequence,
wherein the 5' element of the splint sequence hybridizes to the 5' terminal sequence of the second single-stranded oligonucleotide, and
wherein the 3' element of the splint sequence hybridizes to the 3' terminal sequence of the first single-stranded oligonucleotide,
(4) an optional second spacer sequence, and
(5) a 3' terminal sequence which is the first index sequence.

Embodiment 26. The method of Embodiment 25, wherein each spacer sequence independently consists of 1 to 30 nucleotides.

Embodiment 27. The method of Embodiment 21, 22, or 23, wherein:
(1) the first index sequence is located at the 5' end of the indexed splint; and
(2) the second index sequence is located at the 3' end of the indexed splint.

Embodiment 28. The method of Embodiment 27, wherein:
(a) the first single-stranded oligonucleotide comprises from 5' to 3':
(1) a third index sequence comprising the 5' terminal sequence of the first single-stranded oligonucleotide, and
(2) a first DNA sequence component to be ligated into the multicomponent ligation product, the first DNA sequence component comprising the 3' terminal sequence of the first single-stranded oligonucleotide; and
(b) the second single-stranded oligonucleotide comprises from 5' to 3':
(1) a second DNA sequence component to be ligated into the multicomponent ligation product comprising the 5' terminal sequence of the second single-stranded oligonucleotide and
(2) a fourth index sequence comprising 3' terminal sequence of the second single-stranded oligonucleotide; and
(c) the indexed splint comprises from 5' to 3':
(1) a 5' terminal sequence which is the first index sequence,
(2) an optional first spacer sequence,
(3) the splint sequence,
wherein the 5' element of the splint sequence hybridizes to the 5' terminal sequence of the second single-stranded oligonucleotide, and
wherein the 3' element of the splint sequence hybridized to the 3' terminal sequence of the first single-stranded oligonucleotide,
(4) an optional second spacer sequence, and
(5) a 3' terminal sequence which is the second index sequence.

Embodiment 29. The method of Embodiment 27 or 28, wherein each spacer sequence independently consists of 1 to 30 nucleotides.

Embodiment 30. The method of any one of Embodiments 21 to 29, wherein each double-stranded index element comprises 10 to 40 base pairs.

Embodiment 31. The method of any one of Embodiments 21 to 30, wherein each double-stranded index element has a melting temperature (Tm) from about 10° C. to about 80° C., wherein $$Tm=(2*(A_{count}+T_{count}))+(4*(C_{count}+G_{count}))-7.$$

Embodiment 32. The method of any one of Embodiments 20 to 31, further comprising
(C) denaturing the indexed splint from the multicomponent ligation product, and subsequently performing steps (A), (B) and (C) iteratively.

Embodiment 33. The method of any one of Embodiments 20 to 32, wherein the fourth index sequence is removably (or detachably) linked to the second DNA sequence component.

Embodiment 34. The method of Embodiment 33, wherein the second single-stranded oligonucleotide further comprises a Type IIs restriction enzyme site 3' to the second DNA sequence component, wherein the site of restriction enzyme cleavage is immediately 3' of the second DNA sequence component.

Embodiment 35. The method of Embodiment 33, wherein the fourth index sequence is linked to the second DNA sequence component by a cleavable (or detachable) linker, wherein the site of cleavage is immediately 3' of the second DNA sequence component.

Embodiment 36. The method of any one of Embodiments 33 to 35, further comprising:
  removing the fourth index sequence from the second DNA component in the first ligation product,
  providing a further second single-stranded oligonucleotide having the fourth index sequence, and a further indexed splint comprising a second splint sequence,
  subsequently performing steps (A), (B) and (C),
  wherein the first ligation product is the first single-stranded oligonucleotide of step (A), and
  wherein the second splint sequence of the further indexed splint contains a 5' element that hybridizes to a 5' terminal sequence in the further second single-stranded oligonucleotide and a 3' element that hybridizes to a 3' terminal sequence of the first ligation product.

Embodiment 37. The method of any one of Embodiments 33 to 35, wherein the indexed splint further comprises a second splint sequence adjacent to a fifth index sequence, wherein the 5' element of the second splint sequence can hybridize to the 3' terminal sequence of the second DNA sequence component.

Embodiment 38. The method of any one of Embodiments 20 to 32, wherein the third index sequence is removably (or detachably) linked to the first DNA sequence component.

Embodiment 39. The method of Embodiment 38, wherein the first single-stranded oligonucleotide further comprises a Type IIs restriction enzyme site 5' to the first DNA sequence component, wherein the site of restriction enzyme cleavage is immediately 5' of the first DNA sequence component.

Embodiment 40. The method of Embodiment 38, wherein the third index sequence is linked to the first DNA sequence component by a cleavable (or detachable) linker, wherein the site of cleavage is immediately 5' of the first DNA sequence component.

Embodiment 41. The method of any one of Embodiments 38 to 40, further comprising:
  removing the third index sequence from the first DNA sequence component in the first ligation product,
  providing a further first single-stranded oligonucleotide having the third index sequence, and a further indexed splint,
  subsequently performing steps (A), (B) and (C),
  wherein the first ligation product is the second single-stranded oligonucleotide of step (A), and
  wherein the splint sequence of the further indexed splint contains a 3' element that hybridizes to a 3' terminal sequence in the further first single-stranded oligonucleotide and a 5' element that hybridizes to (is the reverse complement to) a 5' terminal sequence in the first ligation product.

Embodiment 42. The method of any one of Embodiments 20 to 41, wherein:
  the hybridizing step is performed at in a range of temperatures based on the melting temperature (Tm) of the index elements, and
  the ligating step is performed at a temperature that is higher than the melting temperature (Tm) of the 5' and the 3' elements of the splint sequence and lower than the melting temperature (Tm) of the index elements.

Embodiment 43. The method of any one of Embodiments 20 to 42, where the temperature of the ligation step is about 45° to 70° C. and the ligase is thermostable.

Embodiment 44. The method of any one of Embodiments 20 to 43, wherein the melting temperature of the index elements about 60° to 90° C.

Embodiment 45. The method of any one of Embodiments 20 to 44, wherein the melting temperature of the 5' splint element and the 3' splint element is about 20° to 42° C.

The foregoing description of exemplary or preferred embodiments should be taken as illustrating, rather than as limiting, the present disclosure as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following claims. All references cited herein are incorporated by reference in their entireties.

We claim:

1. A method for assembling two nucleic acid components to produce a multicomponent ligation product, comprising;
  (A) hybridizing a first single-stranded oligonucleotide comprising a first DNA sequence component and a second single-stranded oligonucleotide comprising a second DNA sequence component to an indexed splint, wherein both the 5' end and the 3' end of the first single stranded oligonucleotide are hybridized to the indexed splint and both the 5' end and the 3' end of the second single-stranded oligonucleotide are hybridized to the indexed splint; and
  (B) ligating the 3' end of the first single-stranded oligonucleotide to the 5' end of the second single-stranded oligonucleotide, thereby producing a first multicomponent ligation product;
  wherein the indexed splint comprises from 5' to 3':
    (a) a second index sequence,
    (b) a first spacer sequence which does not hybridize to sequences within the first and the second single-stranded oligonucleotides,
    (c) a splint sequence comprising a 5' element and a 3' element,
      wherein the 5' element of the splint sequence hybridizes to the 5' terminal sequence of the second single-stranded oligonucleotide, and
      wherein the 3' element of the splint sequence hybridizes to the 3' terminal sequence of the first single-stranded oligonucleotide,
    (d) a second spacer sequence which does not hybridize to sequences within the first and second single-stranded oligonucleotides, and
    (e) a first index sequence.

2. The method of claim 1, wherein the first index sequence hybridizes to the 5' end of the first single-stranded oligonucleotide to form a first double-stranded index element, and the second index sequence hybridizes to the 3' end of the second single-stranded oligonucleotide to form a second double-stranded index element.

3. The method of claim 1, wherein the 5' element and the 3' element of the splint sequence are contiguous, i.e., without intervening nucleotides.

4. The method of claim 1, wherein:
(1) the first index sequence is located at the 3' end of the indexed splint; and
(2) the second index sequence is located at the 5' end of the indexed splint.

5. The method of claim 4, wherein:
(a) the first single-stranded oligonucleotide comprises from 5' to 3':
(1) a third index sequence comprising a 5' terminal sequence of the first single-stranded oligonucleotide, and
(2) the first DNA sequence component to be ligated into the multicomponent ligation product, the first DNA sequence component comprising the 3' terminal sequence of the first single-stranded oligonucleotide; and
(b) the second single-stranded oligonucleotide comprises from 5' to 3':
(1) the second DNA sequence component to be ligated into the multicomponent ligation product comprising the 5' terminal sequence of the second single-stranded oligonucleotide and
(2) a fourth index sequence comprising a 3' terminal sequence of the second single-stranded oligonucleotide.

6. The method of claim 1, wherein the first spacer sequence and the second spacer sequence consists of 1 to 30 nucleotides.

7. The method of claim 1, wherein:
(1) the first index sequence is located at the 5' end of the indexed splint; and
(2) the second index sequence is located at the 3' end of the indexed splint.

8. The method of claim 7, wherein:
(a) the first single-stranded oligonucleotide comprises from 5' to 3':
(1) a third index sequence comprising a 5' terminal sequence of the first single-stranded oligonucleotide, and
(2) a first DNA sequence component to be ligated into the multicomponent ligation product, the first DNA sequence component comprising the 3' terminal sequence of the first single-stranded oligonucleotide; and
(b) the second single-stranded oligonucleotide comprises from 5' to 3':
(1) a second DNA sequence component to be ligated into the multicomponent ligation product comprising the 5' terminal sequence of the second single-stranded oligonucleotide and
(2) a fourth index sequence comprising a 3' terminal sequence of the second single-stranded oligonucleotide.

9. The method of claim 2, wherein the first double-stranded index element and the second double-stranded index element comprise 10 to 40 base pairs.

10. The method of claim 1, further comprising
(C) denaturing the indexed splint from the multicomponent ligation product, and subsequently performing steps (A), (B), and (C), iteratively;
wherein steps (A), (B), and (C) are repeated with the first single-stranded oligonucleotides, the second single-stranded oligonucleotides, and the indexed splint, or steps (A), (B), and (C) are repeated with different single-stranded oligonucleotides and a different index splint.

11. The method of claim 5, wherein the fourth index sequence is removably linked to the second DNA sequence component.

12. The method of claim 11, wherein:
a) the second single-stranded oligonucleotide further comprises a Type IIS restriction enzyme site 3' to the second DNA sequence component, wherein the site of restriction enzyme cleavage is immediately 3' of the second DNA sequence component; and/or
b) the fourth index sequence is linked to the second DNA sequence component by a cleavable linker, wherein the site of cleavage is immediately 3' of the second DNA sequence component.

13. The method of claim 11, further comprising:
removing the fourth index sequence from the second DNA component in a first ligation product,
providing a further second single-stranded oligonucleotide having the fourth index sequence, and a further indexed splint comprising a second splint sequence, and
subsequently performing steps (A), (B), and (C),
wherein the first ligation product is the first single-stranded oligonucleotide of step (A), and
wherein the second splint sequence of the further indexed splint contains a 5' element that hybridizes to a 5' terminal sequence in the further second single-stranded oligonucleotide and a 3' element that hybridizes to a 3' terminal sequence of the first ligation product.

14. The method of claim 11, wherein the indexed splint further comprises a second splint sequence adjacent to a fifth index sequence, wherein the second splint sequence comprises a 5' element that can hybridize to the 3' terminal sequence of the second DNA sequence component.

15. The method of claim 5, wherein the third index sequence is removably linked to the first DNA sequence component.

16. The method of claim 15, wherein:
a) the first single-stranded oligonucleotide further comprises a Type IIS restriction enzyme site 5' to the first DNA sequence component, wherein the site of restriction enzyme cleavage is immediately 5' of the first DNA sequence component; and/or
b) the third index sequence is linked to the first DNA sequence component by a cleavable linker, wherein the site of cleavage is immediately 5' of the first DNA sequence component.

17. The method of claim 15, further comprising:
removing the third index sequence from the first DNA sequence component in a first ligation product,
providing a further first single-stranded oligonucleotide having the third index sequence, and a further indexed splint,
subsequently performing steps (A), (B) and (C),
wherein the first ligation product is the second single-stranded oligonucleotide of step (A), and
wherein the splint sequence of the further indexed splint contains a 3' element that hybridizes to a 3' terminal sequence in the further first single-stranded oligonucleotide and a 5' element that hybridizes to a 5' terminal sequence in the first ligation product.

18. The method of claim 2, wherein:
a) the hybridizing step is performed in a range of temperatures based on the melting temperature (Tm) of the first and the second double-stranded index element, and the ligating step is performed at a temperature that is higher than the melting temperature (Tm) of the 5' and the 3' elements of the splint sequence and lower than the melting temperature (Tm) of the first and the second double-stranded index elements;
b) the temperature of the ligation step is about 45° to 70° C. and the ligase is thermostable;
c) the melting temperature of the first and the second double-stranded index elements is about 60° to 90° C.; and/or
d) the melting temperature of the 5' and the 3' elements of the splint sequence is about 20° to 42° C.

19. The method of claim 1, further comprising digesting the first single-stranded oligonucleotide or the second single-stranded oligonucleotide at the 5' end using an exonuclease.

\* \* \* \* \*